(12) United States Patent
Goral

(10) Patent No.: US 11,345,880 B2
(45) Date of Patent: May 31, 2022

(54) 3D CELL CULTURE VESSELS FOR MANUAL OR AUTOMATIC MEDIA EXCHANGE

(71) Applicant: CORNING INCORPORATED, Corning, NY (US)

(72) Inventor: Vasiliy Nikolaevich Goral, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 55 days.

(21) Appl. No.: 16/628,375

(22) PCT Filed: Jul. 13, 2018

(86) PCT No.: PCT/US2018/042159
§ 371 (c)(1),
(2) Date: Jan. 3, 2020

(87) PCT Pub. No.: WO2019/014635
PCT Pub. Date: Jan. 17, 2019

(65) Prior Publication Data
US 2020/0181553 A1    Jun. 11, 2020

Related U.S. Application Data

(60) Provisional application No. 62/532,639, filed on Jul. 14, 2017.

(51) Int. Cl.
*C12M 3/06* (2006.01)
*C12M 1/24* (2006.01)
(Continued)

(52) U.S. Cl.
CPC ............ *C12M 23/16* (2013.01); *C12M 23/08* (2013.01); *C12M 23/12* (2013.01); *C12M 23/44* (2013.01)

(58) Field of Classification Search
CPC ...... C12M 23/16; C12M 23/08; C12M 23/12; C12M 23/44
See application file for complete search history.

(56) References Cited

U.S. PATENT DOCUMENTS 2,947,116 A    8/1960   Earle et al.
3,630,849 A   12/1971   Land et al.
(Continued)

FOREIGN PATENT DOCUMENTS

AU    2004256209 A1   1/2005
CA       2558946 A1   1/2005
(Continued)

OTHER PUBLICATIONS

European Patent Application No. 18749952.0 Office Action dated Nov. 17, 2020; 4 pages; European Patent Office.
(Continued)

*Primary Examiner* — Michael L Hobbs
(74) *Attorney, Agent, or Firm* — Annie J. Morgan

(57) ABSTRACT

A cell culture vessel (400) includes a base defining a base plane extending in a first direction and a second direction perpendicular to the first direction, a plurality of cell culture chambers (200) stacked one atop another, each cell culture chamber having a top (202), a bottom (201) and sidewalls (203), each of the top, bottom and sidewalls having an interior surface, wherein at least the bottom surface has an array of microcavities (420) supporting the culture of cells as spheroids and each bottom surface is at an angle with respect to the plane of a table or surface upon which the vessel sits. Further, liquid can flow into each cell culture chamber via an inlet (210) and out of each cell culture chamber via an outlet (215). The angled cell culture surface
(Continued)

allows the cell culture chambers to be perfused or allows media changes without dislodging spheroids from microcavities.

29 Claims, 12 Drawing Sheets

(51) Int. Cl.
  *C12M 1/32* (2006.01)
  *C12M 3/00* (2006.01)

(56) References Cited

U.S. PATENT DOCUMENTS

| | | |
|---|---|---|
| 4,670,396 A | 6/1987 | Bear et al. |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,374,557 A | 12/1994 | Verma |
| 5,487,872 A | 1/1996 | Hafeman et al. |
| 5,554,536 A | 9/1996 | Rising |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 * | 5/2003 | Rosen ............... H04M 1/27485 455/564 |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 2002/0022219 A1 | 2/2002 | Clements et al. |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2005/0032208 A1 | 2/2005 | Oh et al. |
| 2005/0047971 A1 | 3/2005 | Clements et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0299649 A1 | 12/2008 | Martin et al. |
| 2008/0300278 A1 | 12/2008 | Torrens Jover et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0093075 A1 | 4/2010 | Muller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2012/0064627 A1 | 3/2012 | Khine et al. |
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |

(56) References Cited

U.S. PATENT DOCUMENTS

| | | |
|---|---|---|
| 2013/0164848 A1 | 6/2013 | Munaka et al. |
| 2013/0203159 A1 | 8/2013 | Itoh et al. |
| 2013/0344598 A1 | 12/2013 | Nistor |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0227784 A1 | 8/2014 | Ejiri et al. |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0283757 A1 | 10/2017 | Carter et al. |
| 2017/0306281 A1 | 10/2017 | Martin et al. |
| 2017/0342363 A1 | 11/2017 | Fang et al. |
| 2018/0201888 A1 | 7/2018 | Miwa et al. |
| 2020/0239854 A1 | 7/2020 | Ayano et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1234112 A | 11/1999 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| DE | 8309876 U1 | 12/1983 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 307048 A2 | 3/1989 |
| EP | 0605527 A1 | 7/1994 |
| EP | 0681846 A2 | 11/1995 |
| EP | 0800571 A2 | 10/1997 |
| EP | 834552 A1 | 4/1998 |
| EP | 965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 06327462 A | 11/1994 |
| JP | 09173049 A | 7/1997 |
| JP | 09-234811 A | 9/1997 |
| JP | 10210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004129558 A | 4/2004 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2009-542230 A | 12/2009 |
| JP | 2010088347 A | 4/2010 |
| JP | 2010104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2012249547 A | 12/2012 |
| JP | 2013055911 A | 3/2013 |
| JP | 2014132869 A | 7/2014 |
| JP | 2015012827 A | 1/2015 |
| JP | 2015073520 A | 4/2015 |
| JP | 5845185 B2 | 1/2016 |
| JP | 2016136921 A | 8/2016 |
| JP | 2017-532970 A | 11/2017 |
| KR | 1020140113139 A | 9/2014 |
| KR | 10-2014-0125662 A | 10/2014 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008118500 A1 | 10/2008 |
| WO | 2008153783 A1 | 12/2008 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2010/042072 A1 | 4/2010 |
| WO | 2010/069589 A1 | 6/2010 |
| WO | 2012036011 A1 | 3/2012 |
| WO | 2012170232 A1 | 12/2012 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |

(56) References Cited

FOREIGN PATENT DOCUMENTS

| | | |
|---|---|---|
| WO | 2014196204 A1 | 12/2014 |
| WO | 2015033507 A1 | 3/2015 |
| WO | 2015/061907 A1 | 5/2015 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 A1 | 5/2016 |
| WO | 2017025584 A1 | 2/2017 |
| WO | 2017/047735 A1 | 3/2017 |
| WO | 2017/077163 A1 | 5/2017 |
| WO | 2017142410 A1 | 8/2017 |
| WO | 2018200893 A1 | 11/2018 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

Lovett et al. "Vascularization Strategies for Tissue Engineering" Tissue Engineering Part B, 2009, vol. 15, No. 3, pp. 353-370.
Office Action dated Aug. 8, 2019 pertaining to U.S. Appl. No. 15/708,473, filed Sep. 19, 2017, 20 pgs.
Achilli et al., "Advances in the Formation, Use and Understanding of Multi-Cellular Spheroids", Expert Opin. Biol. Ther. (2012) 12(10):1347-1360.
Alepee et al, "State-of-the-Art 3D Cultures (Organs-on-a-Chip) in Safety Testing and Pathophysiology"; Transatlantic Think Tank for Toxicology, T4 Workshop Report, Altex 31, Apr. 2014, pp. 441-477, Retrieved From: http://dx.doi.org/10.14573/altex1406111 (Jul. 14, 2014).
Aline, "We Engineer Microfluidic Products"; 7 Pages; (2020) https://alineinc.com/.
G-Plate: Accelerate your cell cultures to the next dimension, "An original cell culture model allowing for island-shaped 3D cell aggregates", 1 page, retrieved Sep. 8, 2015.
Anada et al, "An Oxygen-Permeable Spheroid Culture System for the Prevention of Central Hypoxia and Necrosis of Spheroids"; Biomaterials 33 (2012) 8430-8441.
Bartosh et al, "Aggregation of Human Mesenchymal Stromal Cells (MSCS) Into 3D Spheroids Enhances Their Antiinflammatory Properties"; PNAS, Aug. 3, 2010, 107 (31):13724-13729.
Bioivt Elevating Science®; 6 Pages; (2020); http://www.hepregen.com/.
Carver et al, "Multicellular Tumor Spheroids as a Model for Assessing Delivery of Oligonucleotides in Three Dimensions"; Molecular Therapy-Nucleic Acids (2014) 3, E153; 8 Pages.
Chen et al, "Microfluidic array for three-dimensional perfusion culture of human mammary epithelial cells" Biomedical Microdevices, 2011, 13(4):753-758.
Cheng et al, "MICRORNA-34a Targets Forkhead Box J2 To Modulate Differentiation of Endothelial Progenitor Cells in Response To Shear Stress", J Mol Cell Cardiol. 74 (2014) 4-12.
Choi et al, "Feasibility of a simple double-layered coculture system incorporating metabolic processes of the intestine and liver tissue: application to the analysis of benzo[a]pyrene toxicity", Toxicology in Vitro 18 (2004) 393-402.
CN-BIO, "Transforming Drug Discovery and the Lives of Patients"; 5 Pages; (2020) http://cn-bio.com/.
Colazzo et al, "Shear Stress and VEGF Enhance Endothelial Differentiation of Human Adipose-Derived Stem Cells", Growth Factors, 2014, 32(5):139-149.
Corning® HTS Transwell®-96 Tissue Culture Systems, Permeable Supports for High Throughput Screening Applications; 2 Pages (2004).
Tissue Dynamics, "Disruptive Drug Development"; 3 Pages; (Downloaded Mar. 9, 2020); https://www.tissuedynamics.com/.

Dolznig et al, "Organotypic spheroid cultures to study tumor-stroma interaction during cancer development", Drug Discovery Today: Disease Models, 2011, 8(2-3):113-118.
Domansky et al, "Perfused Multiwell Plate for 3D Liver Tissue Engineering", Lab Chip, 2010, 10:51-58.
Emulate, 6 Pages; (2019) https://emulatebio.com/.
Tissuse, "Emulating Human Biology, Pioneering Human-on-a-Chip Developments"; 1 Page; (Downloaded Mar. 9, 2020) https://www.tissuse.com/en/.
Endo et al, "Gene transfection to spheroid culture system on micropatterned culture plate by polyplex nanomicelle: a novel platform of genetically-modified cell transplantation", Drug Deliv. and Transl. Res., 2012, 2:398-405.
Engelberg et al, "Essential operating principles for tumor spheroid growth", BMC Systems Biology 2008, 2:110, 19 pages.
Friedrich et al, "Experimental anti-tumor therapy in 3-D: spheroids—old hat or new challenge?" Int J Radiat Biol 2007, 83(11-12):849-871.
Friedrich et al, "Spheroid-based drug screen: considerations and practical approach", Nature protocols, 2009, 4(3):309-323.
Frith et al, "Dynamic three-dimensional culture methods enhance mesenchymal stem cell properties and increase therapeutic potential", Tissue engineering, 2010, 16(4):735-749.
Fukuda et al, "Efficacy of a polyurethane foam/spheroid artificial liver by using human hepatoblastoma cell line (Hep G2)", Cell Transplantation, 2003, 12:51-58.
GeoCHEM Incorporated, Product Line; https://www.geocheminc.com, 4 Pages; (2020).
Haycock, "3D cell culture: a review of current approaches and techniques", Methods Mol Biol, 2011; 695:1-15.
Hirschhaeuser et al, "Multicellular tumor spheroids: An underestimated tool is catching up again", Journal of Biotechnology 148 (2010) 3-15.
Howes et al, "3-Dimensional Culture Systems for Anti-Cancer Compound Profiling and High-Throughput Screening Reveal Increases in EGFR Inhibitor-Mediated Cytotoxicity Compared to Monolayer Culture Systems"; Plos One; Sep. 2004, 9(9), 11 Pages.
Hribar et al, "Nonlinear 3D Projection Printing of Concave Hydrogel Microstructures for Long-Term Multicellular Spheroid and Embryoid Body Culture"; Lab Chip, 2015, 15, 2412-2418.
Hwang et al, "Microwell-Mediated Control of Embryoid Body Size Regulates Embryonic Stem Cell Fate Via Differential Expression of WNT5A and WNT11"; PNAS, 2009, 106(40):16978-16983.
HμREL® Corporation, Bioanalytic Tools Company; 2 Pages; (2013); http://hurelcorp.com/.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through TAZ Activation" PLoS One, Mar. 21, 2014; 9(3), e92427, 9 pages.
Koide et al, "Formation of multicellular spheroids composed of adult rat hepatocytes in dishes with positively charged surfaces and under other nonadherent environments", Exp Cell Res 1990; 186:227-235.
Kunz-Schughart et al, "The use of 3-D cultures for high-throughput screening: the multicellular spheroid model", J Biomol Screen 2004, 9(4):273-285.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca, "Scaffold free 3D culture of mesenchymal stem cells; implications for regenerative medicine", J Transplant Stem Cel Biol 2015 2(1): 8.

(56) References Cited

OTHER PUBLICATIONS

Landry et al, "Spheroidal aggregate culture of rat liver cells: histotypic reorganization, biomatrix deposition, and maintenance of functional activities" J Cell Biol 1985; 101:914-923.
Lau et al, "Evaluation of a Novel in Vitro CACO-2 Hepatocyte Hybrid System for Predicting in Vivo Oral Bioavailability" Drug Metabolism and Disposition, vol. 32, No. 9, pp. 937-942, 2004.
Liquid Surge Control, LLC; "The Latest in Drop-in Baffle Technology"; 2 Pages; (2019).
Liu et al, "Quasi-spherical microwells on superhydrophobic substrates for long term culture of multicellular spheroids and high throughput assays" Biomaterials 35 (2014) pp. 6060-6068.
Liu et al, "Advanced Micromachining of Concave Microwells for Long Term on-Chip Culture of Multicellular Tumor Spheroids", ACS Appl. Mater. Interfaces, 2014, 6, 8090-8097.
Lu et al, "Galactosylated PVDF membrane promotes hepatocyte attachment and functional maintenance" Biomaterials 24 (2003) 4893-4903.
Markovitz-Bishitz, "A polymer microstructure array for the formation, culturing, and high throughput drug screening of breast cancer spheroids" Biomaterials 31 (2010) 8436-8444.
Messner et al, Multi-cell type human liver microtissues for hepatotoxicity testing. Archives of Toxicology, Nov. 11, 2012, 5 pages.
Elveflow; "Microfluidics Innovation Center"; 6 Pages; (Downloaded Mar. 9, 2020); https://www.elveflow.com/.
Mironov et al, "Organ Printing: Tissue Spheroids as Buliding Blocks" Biomaterials, 2009; 30 (12): 2164-2174.
Moon et al, "Optimizing Human Embryonic Stem Cells Differentiation Efficiency by Screening Size-Tunable Homogenous Embryoid Bodies"; Biomaterials; 35 (2014) 5987-5997.
Urich et al, "Multicellular Self-Assembled Spheroidal Model of the Blood Brain Barrier" Scientific Reports, 3, 1500, 8 Pages.
Murphy et al, "3D Bioprinting of Tissues and Organs"; Nature Biotechnology, vol. 32, No. 8, Aug. 2014, pp. 773-785.
Nortis; "Bridging the Gap Between in Vitro and in Vivo Research"; 16 Pages; (2015); https://www.nortisbio.com/.
Mimetas the Organ-on-a-Chip Company; "Organ-on-a-Chip Models for Science and Pharma"; 4 Pages; (Downloaded Mar. 9, 2020); https://mimetas.com/.
Otsuka et al, "Two-dimensional multiarray formation of hepatocyte spheroids on a microfabricated PEG-brush surface." ChemBioChem 2004; 5:850-855.
Peshwa et al, "Mechanistics of formation and ultrastructural evaluation of hepatocyte spheroids." In Vitro Cell Dev Biol Anim 1996; 32:197-203.
Organovo, "Pioneering Bioprinted Tissues to Treat Disease"; 2 Pages; (Downloaded Mar. 9, 2020) http://organovocom/.
Rezende et al, "Scalable Biofabrication of Tissue Spheroids for Organ Printing"; Sciverse Science Direct, Procedia Cirp 5, (2013) 276-281.
Sa et al, "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Detachably Assembled Microfluidic Device for Perfusion Culture and Post-Culture Analysis of Spheroid Array"; Biotechnol. J. 2014, 9, 971-979.
Sakai et al, "Technique for the Control of Spheroid Diameter Using Microfabricated Chips"; Sciencedirect, Acta Biomaterialia 3 (2007) 1033-1040.
Sart et al, "Three-dimensional aggregates of mesenchymal stem cells: cellular mechanisms, biological properties and applications" Tissue engineering, 2013, Part B, vol. 00, No. 00, 1-16.
Satoh et al, "A Pneumatic Pressure-Driven Multi-Throughput Microfluidic Circulation Culture System" Lab Chip, 2016, 16, 2339-2348.
Seldon et al, "Evaluation of Encapsulated Liver Cell Spheroids in a Fluidised-Bed Bioartificial Liver for Treatment of Ischaemic Acute Liver Failure in Pigs in a Translational Setting"; Plos One, 2013, 8(12), e82312.
Takezawa et al, "Morphological and immuno-cytochemical characterization of a hetero-spheroid composed of fibroblasts and hepatocytes" J Cell Sci 1992; 101:495-501.
Tara; "Innovating Predictive Cardiac Physiology"; 4 Pages; (2019) http://tarabiosystems.com/.
The Lab Depot® Products for Discovery Lab Supplies; Shake Flasks, 3 and 4 Baffles Product Information; 5 Pages (2019).
Tobe et al, "Receptor-mediated formation of multilayer aggregates of primary cultured adult rat hepatocytes on lactose-substituted polystyrene" Biochem Biophys Res Commun 1992; 184(1):225-230.
Tong et al, "Long-term culture of adult rat hepatocyte spheroids." Exp Cell Res 1992; 200:326-332.
Truckenmuller et al, Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136 (3), 473-478.
Uchida et al, "An Injectable Spheroid System With Genetic Modification for Cell Transplantation Therapy"; Biomaterials, 35 (2014) 2499-2506.
Vinci et al, Advances in establishment and analysis of three-dimensional tumor spheroid-based functional assays for target validation and drug evaluation, BMC Biology 2012, 10:29.
Weegman et al, "Nutrient Regulation By Continuous Feeding Removes Limitations on Cell Yield in the Large-Scale Expansion of Mammalian Cell Spheroids"; Plos One, 2013, vol. 8, Issue 10, e76611, 10 Pages.
Wikipedia, "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5):453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.
Yamada et al, "Efficient induction of hepatocyte spheroids in a suspension culture using a water-soluble synthetic polymer as an artificial matrix." J Biochem 1998; 123:1017-1023.
AxoSIM, Nerve-on-a-Chip Mini-Brain About Team; 6 Pages; (Downloaded Mar. 9, 2020); http://axosim.com/.
Corning Life Sciences Product Portfolio; 5 Pages Saved Mar. 6, 2020.
Madoux et al, "Building Phenotypic 3D Spheroid HTS Assays to Identify Synthetic Lethal Small Molecule Inhibitors of KRAS"; the Scripps Research Institute Molecular Screening Center and Department of Cancer Biology, Scripps Florida, Jupiter, Florida, Department of Pathology, Jupiter Medical Center, Jupiter, Florida.
Stemcell Technologies, Reproducible and Uniform Embryoid Bodies Using AggreWell Plates, StemCell Technologies, Technical Manual Version 3.0.0, Mar. 2011, Catalog #29146, pp. 1-28.
Achilli et al., "Advances In The Formation, Use And Understanding Of Multi-cellular Spheroids", Expert Opinion On Biological Therapy, vol. 12, No. 10, Jul. 2012, pp. 1347-1360.
Brandrup et al., "Polymer Handbook", Fourth Edition, Wiley-Interscience Publication, , Permeability and diffusion data, 1999, 9 pages (Contributors; Preface).
Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Hsiao et al., "Effects of 3D Microwell Culture on Initial Fate Specification in Human Embryonic Stem Cells", Published in final edited form as AIChE J. vol. 60 No. 4, Apr. 2014, pp. 1225-1235.
Junji Fukuda et al., "Hepatocyte Spheroid Arrays Inside Microwells Connected With Microchannels", Biomicrofluidics 5, 2011, p. 10.
Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.

(56) References Cited

OTHER PUBLICATIONS

Martin et al., "Agarose And Methylcellulose Hydrogel Blends For Nerve Regeneration Applications", J. Neural Eng., vol. 5, 2008, pp. 221-231.
Polyimide: Japan Polyimide and Aromatic Polymers Study Group, 2010, pp. 364-371 Table 2.
Yang et al.,"An Agarose-Gel Based Method for Transporting Cell Lines", Current Chemical Genomics, vol. 3, Jan. 2009, pp. 50-53.
Zuidema et al., "Fabrication And Characterization Of Tunable Polysaccharide Hydrogel Blends For Neural Repair", Acta Biomaterialia, vol. 7, No. 4, Apr. 2011, pp. 1634-1643.

\* cited by examiner

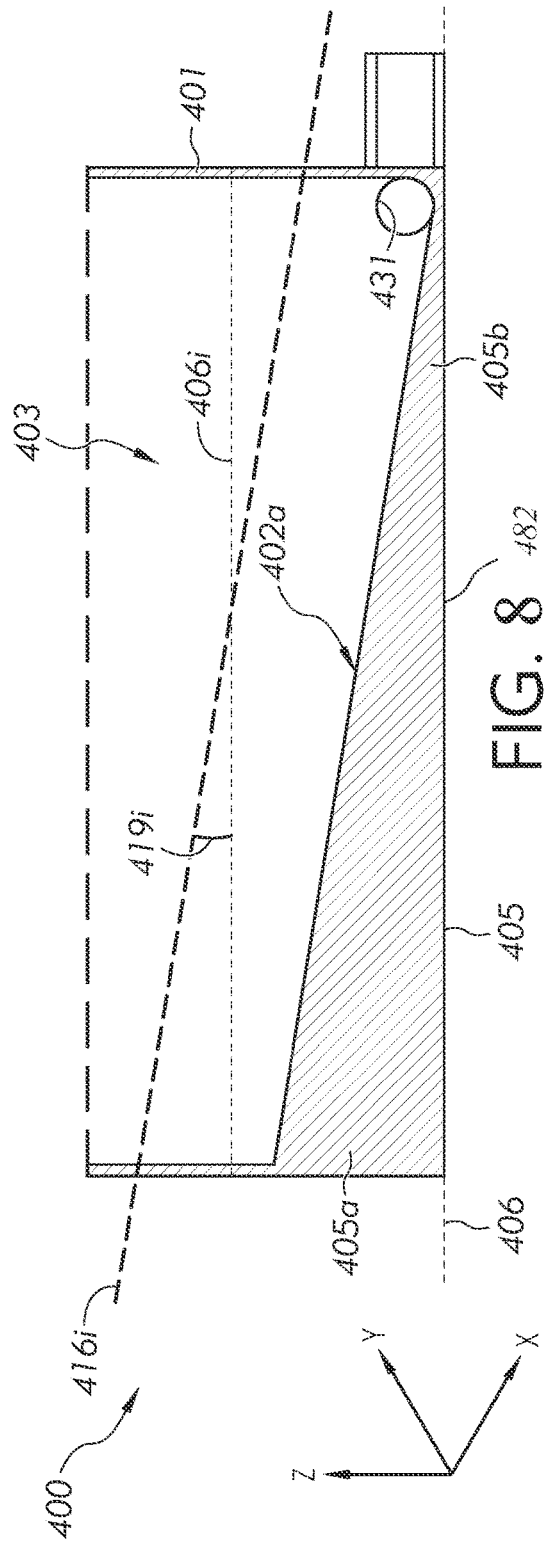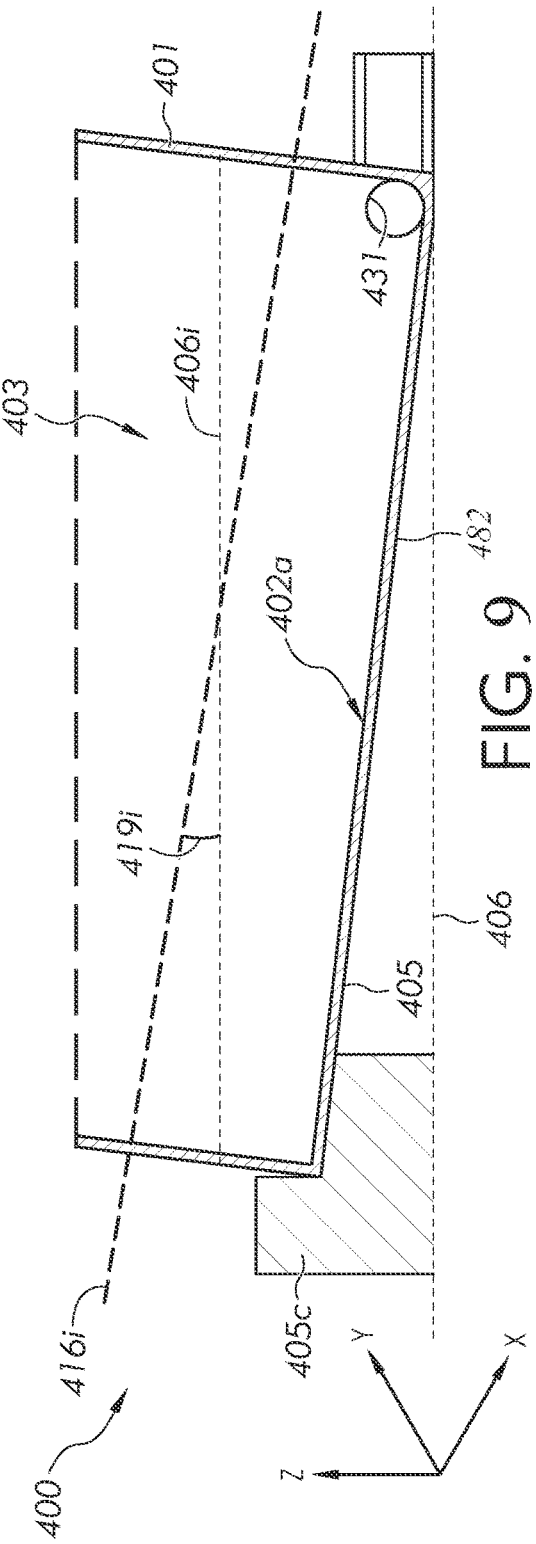

3D CELL CULTURE VESSELS FOR MANUAL OR AUTOMATIC MEDIA EXCHANGE

CROSS REFERENCE TO RELATED APPLICATION

This is a national stage application under 35 U.S.C. § 371 of International Application No. PCT/US2018/042159 filed on Jul. 13, 2018, which claims the benefit of priority of U.S. Provisional Application Ser. No. 62/532,639 filed on Jul. 14, 2017, entitled "Cell Culture Containers and Methods of Culturing Cells", the content of which are relied upon and incorporated herein by reference in their entireties.

FIELD

The present disclosure relates generally to a cell culture vessel and methods of culturing cells, and more particularly, to a cell culture vessel for containing and basing three-dimensional cell culture, including exchanging media, and methods of culturing three-dimensional cells and methods of exchanging media using the cell culture vessel.

BACKGROUND

It is known to contain three-dimensional cells in a cell culture vessel. It is also known to culture three-dimensional cells in a cell culture vessel.

SUMMARY

The following presents a simplified summary of the disclosure in order to provide a basic understanding of some exemplary embodiments described in the detailed description.

A cell culture vessel (e.g., flask) can provide a sterile microcavity for culturing cells. In some embodiments, culturing cells can provide information related to the study of diseases and toxicology, the efficacy of medications and treatments, characteristics of tumors, organisms, genetics, and other scientific, biological, and chemical principles of and relating to cells. The cell culture vessel provides a sterile, liquid-impermeable microcavity to contain cells during culture.

The microcavity or cell growth chamber can include a bottom surface, a top surface and sidewalls having surfaces. At least one of these surfaces can be adapted for cell growth. For example, to base the culture of spheroid cells, the cell growth surface can include a plurality of microcavities (e.g., micron-sized wells, submillimeter-sized wells) arranged, for example, in an array. The cell growth surface can be integral to the flask or can be a separate substrate placed or affixed in the cell growth chamber. The top surface, the bottom surface, one or more side surfaces or a combination of these can include microcavities in an array. Microcavities can be, for example, formed in an undulating or sinusoidal shape forming microcavities or microwells having rounded tops and rounded bottoms. In some embodiments, the flask can be filled with a material (e.g., media, solid, liquid, gas) that facilitates growth of three-dimensional cell cultures (e.g., cell aggregates, spheroids). For example, a media including cells suspended in a liquid can be added to the cell culture chamber. The suspended cells can collect in the plurality of microcavities and can form (e.g., grow) into grouping or cluster of cells. The grouped or clustered cells grow in three dimensions to form cells in 3D, otherwise known as a spheroid or an organoid. A single cluster of cells or spheroid forms in a single microcavity. Thus, a cell culture chamber, having a cell culture surface having an array of microcavities, can be used to culture an array of spheroids, each residing in its own microcavity.

For example, in some embodiments, a single spheroid can form in each microcavity of the plurality of microcavities. Cells will settle into a microcavity by gravity. One or more cells suspended in liquid media will fall through the liquid and settle within each microcavity. The shape of the microcavity (e.g., a concave surface defining a well), and a surface coating of the microcavity that prevents the cells from attaching to the surface can also facilitate growth of cells into three-dimensional form, forming a spheroid in each microcavity.

During culturing, the spheroids can consume media (e.g., food, nutrients) and produce metabolites (e.g., waste) as a byproduct. Thus, in some embodiments food in the form of media can be added to the cell culture chamber during culturing and waste media can be removed from the cell culture chamber during culturing. This ability to change the media to feed cells and remove waste products, promotes the long-term culture of cells. However, adding and removing media may displace spheroids resting in microcavities. This is especially true when the microcavities are coated with a low binding coating to prevent the cells from sticking to the microcavity surface. In this disclosure, structures are disclosed which reduce the risk of displacing spheroids from the microcavities, thus promoting the long-term culture of spheroids. As compared to two-dimensional cell cultures, in some embodiments, three-dimensional cell cultures can produce multicellular structures that are more physiologically accurate and that more realistically represent an environment in which cells can exist and grow in real life applications as compared to simulated conditions in a laboratory. For example, three-dimensional cell cultures have been found to more closely provide a realistic environment simulating "in vivo" (i.e. within the living, in a real-life setting) cell growth; whereas two-dimensional cell-cultures have been found to provide an environment simulating "in vitro" (i.e., within the glass, in a laboratory setting) cell growth that is less representative of a real-life environment occurring outside of a laboratory. By interacting with and observing the properties and behavior of three-dimensional cell cultures, advancements in the understanding of cells relating to, for example, the study of diseases and toxicology, the efficacy of medications and treatments, characteristics of tumors, organisms, genetics, and other scientific, biological, and chemical principles of and relating to cells can be achieved.

In some embodiments, it is desirable to culture large numbers of spheroids for long periods of time in order to amplify signals during the study of diseases and toxicology, the efficacy of medications and treatments, characteristics of tumors, organisms, genetics and other scientific, biological, and chemical principles of and relating to cells. For example, if it is desired to test for metabolites of a drug, it may be necessary to culture cells for a long period of time in order give the cultured cells time enough to metabolize the drug in sufficient quantity for the metabolite to be measurable. In some embodiments, it is also desirable to grow large numbers of spheroids in as small a physical space as possible, to economize space in incubators during cell culture. Single layer cell culture devices, including flasks, are known in the art. Multilayer cell culture devices, which allow a user to culture more cells per cubic inch of incubator space are also known; see, for example, U.S. Pat. Nos. 7,745,209, 8,273,572, 8,470,589, 8,846,399, 9,045,721, 9,845,451 and 8,178,345, all assigned to Corning Incorporated. FIG. 1 is taken from U.S. Pat. No. 8,178,345 and is provided as an illustration of the prior art. Multi-layer devices structured and arranged to grow spheroid cells have been disclosed (see, for example, WO2016/069885 and WO2016/069892, also assigned to Corning Incorporated). All cited references are herein incorporated by reference. The present disclosure provides a single-layer or multi-layer cell culture vessel adapted to reduce the risk of displacing spheroids, resting in microcavities, during media changes.

In embodiments, a cell culture vessel includes a base defining a base plane extending in a first direction and a second direction perpendicular to the first direction. In embodiments, the cell culture vessel has a plurality of cell culture chambers stacked one atop another, each cell culture chamber having a top, a bottom and sidewalls to form a cell culture chamber. Each of the top, bottom and sidewalls have an interior surface facing the inside of the cell culture chamber. In embodiments, at least the bottom surface has an array of microcavities for basing the culture of cells as spheroids. In embodiments, each bottom surface of each cell culture chamber is at an angle with respect to the base plane. Further, liquid can flow through into each cell culture chamber via an inlet and out of each cell culture chamber via an outlet. The angled cell culture surface prevents spheroids from being dislodged during media changes.

In embodiments, a cell culture vessel can include one or more cell culture chambers. Each cell culture chamber (defined by a top, sidewalls and a bottom) has at least a bottom surface that has an array of microcavities to allow cells to grow in 3D or spheroid formation in the cell culture chambers. In addition, the vessel has a table plane, perpendicular to the direction of gravity, the plane extending in a first direction, and a second direction perpendicular to the first direction. The table plane is parallel to the plane of the surface upon which the vessel sits. The table plane is, for example the flat plane of a table or workspace upon which the vessel sits. The bottom surface of each cell culture chamber can be oriented at a first angle relative to the first direction of the table plane, and at a second angle relative to the second direction of the table plane. In embodiments, an absolute value of at least one of the first angle and the second angle can be greater than zero. In some embodiments, a method can include culturing cells in the cell culture vessel.

In some embodiments, a method of culturing cells can include introducing liquid into a plurality of cell culture chambers while a base plane of the vessel is oriented perpendicular relative to the direction of gravity. The base plane can extend in a first direction and a second direction perpendicular to the first direction. The method can include culturing cells in the at least one cell culture chamber after introducing the liquid into the at least one chamber, and flowing liquid in a flow direction parallel to the substrate plane while culturing the cells in the at least one microcavity.

The above embodiments are exemplary and can be provided alone or in any combination with any one or more embodiments provided herein without departing from the scope of the disclosure. Moreover, it is to be understood that both the foregoing general description and the following detailed description present embodiments of the present disclosure, and are intended to provide an overview or framework for understanding the nature and character of the embodiments as they are described and claimed. The accompanying drawings are included to provide a further understanding of the embodiments, and are incorporated into and constitute a part of this specification. The drawings illustrate various embodiments of the disclosure, and together with the description, serve to explain the principles and operations thereof.

BRIEF DESCRIPTION OF THE DRAWINGS

These and other features, embodiments, and advantages of the present disclosure can be further understood when read with reference to the accompanying drawings in which:

FIG. 8 shows an alternative exemplary embodiment of a portion of the cell culture vessel taken at view 8 of FIG. 7 including a base including a thicker portion and a thinner portion in accordance with embodiments of the disclosure;

FIG. 9 shows an alternative exemplary embodiment of a portion of the cell culture vessel taken at view 8 of FIG. 7 including a base including a base in accordance with embodiments of the disclosure;

DETAILED DESCRIPTION

Figure 1:
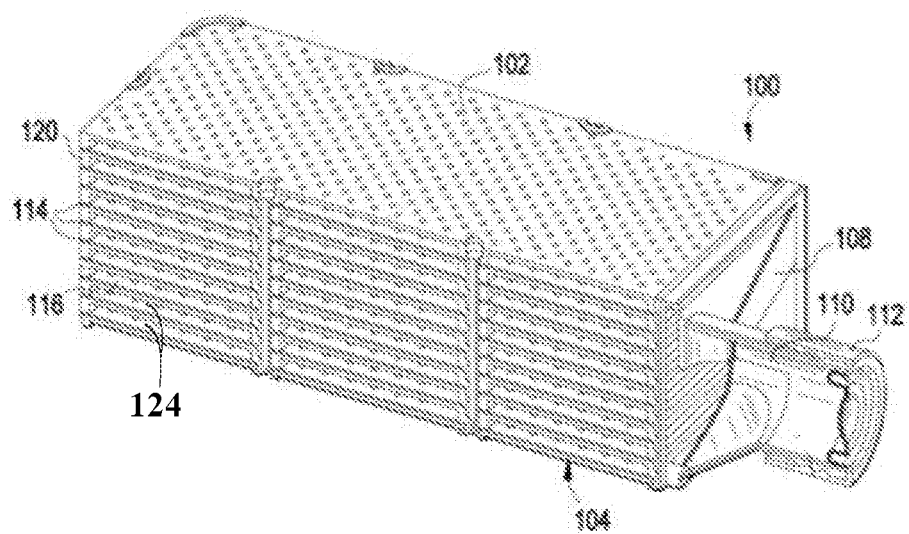
FIG. 1 represents the PRIOR ART and shows a cut-away view of a multilayer cell culture vessel.

Features will now be described more fully hereinafter with reference to the accompanying drawings in which exemplary embodiments of the disclosure are shown. Whenever possible, the same reference numerals are used throughout the drawings to refer to the same or like parts. However, this disclosure can be embodied in many different forms and should not be construed as limited to the embodiments set forth herein.

FIG. 1 represents the PRIOR ART and shows a cut-away view of a multilayer cell culture vessel 100. As illustrated in this PRIOR ART device, a multilayer cell culture vessel is illustrated having a top surface 102 a bottom surface 104, a necked opening 110 with a cap 112, and sidewalls 120. There are a plurality of cell culture chambers 114. The bottom surface 116 of the cell culture chambers 114 are made up of gas permeable, liquid impermeable material which is adjacent to a tracheal space 124. To fill this vessel, a use introduces fluid into the necked opening, distributing liquid into each cell culture chamber via the manifold 108. Perfusion is not possible in this vessel.

Figure 2:
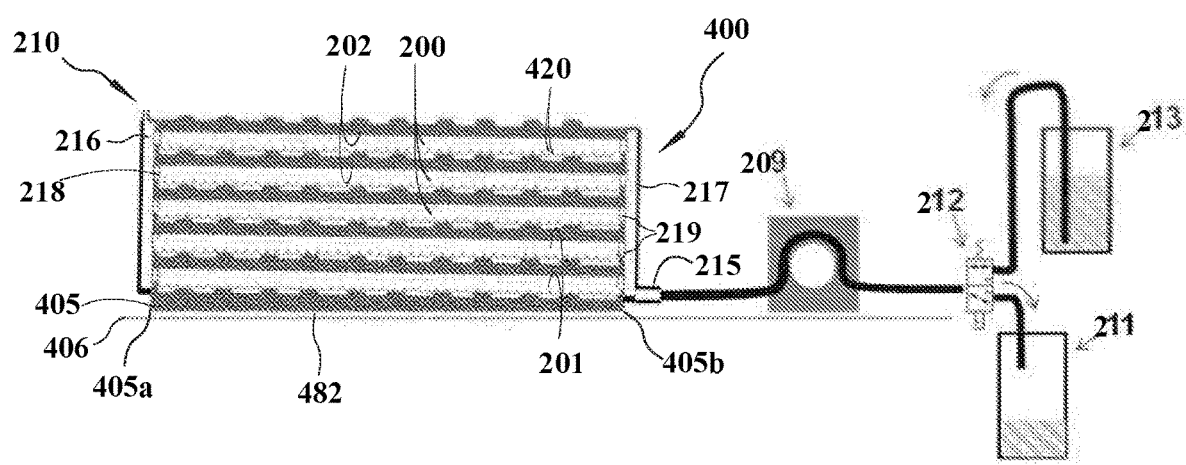
FIG. 2 is a schematic diagram of a perfusion system, in an embodiment of the present disclosure.

FIG. 2 is a schematic diagram of a perfusion system, in an embodiment of the present disclosure. FIG. 2 illustrates a multilayer cell culture vessel 400. The vessel 400 has a top surface 102 and a bottom surface 482. Each layer of the multilayer cell culture vessel is a discrete cell culture chamber 200. Each cell culture chamber has a bottom 201, a top 202, and sidewalls 203 (not shown in FIG. 2) that together define the cell culture chamber 200. Each of the bottom 201, top 202 and sidewalls 203 have an interior surface that face into the cell chamber 200. In embodiments, there are at least two cell culture chambers stacked one above, each having a bottom, a top and sidewalls. In embodiments, at least one of these surfaces has microcavities 420. In embodiments, at least the bottom surface has microcavities 420. In embodiments the microcavities 420 are provided in an array of microcavities. FIG. 2 illustrates an embodiment having five layers of cell culture chambers 200, each cell culture chamber 200 having a bottom 201 having an array of microcavities 420. As used herein, "array" means merely a plurality of microcavities 420.

These microcavities 420 are structured and arranged to provide base for cultured cells to form three dimensional structures, or spheroids. That is, the microcavities 420 are coated with a non-binding coating to keep cells from sticking to the substrate and forming monolayers of cells, and in addition, these microcavities have an appropriate geometry to encourage cells to cluster together and form spheroids in culture. In an embodiment, and as shown in FIGS. 11 and 13-18, these microcavities 420 are sinusoidal in shape. That is, the microcavities 420 have rounded tops and rounded bottoms. However, microcavities 420 can be in any shape or geometry consistent with the formation of spheroids in culture.

Figure 3:
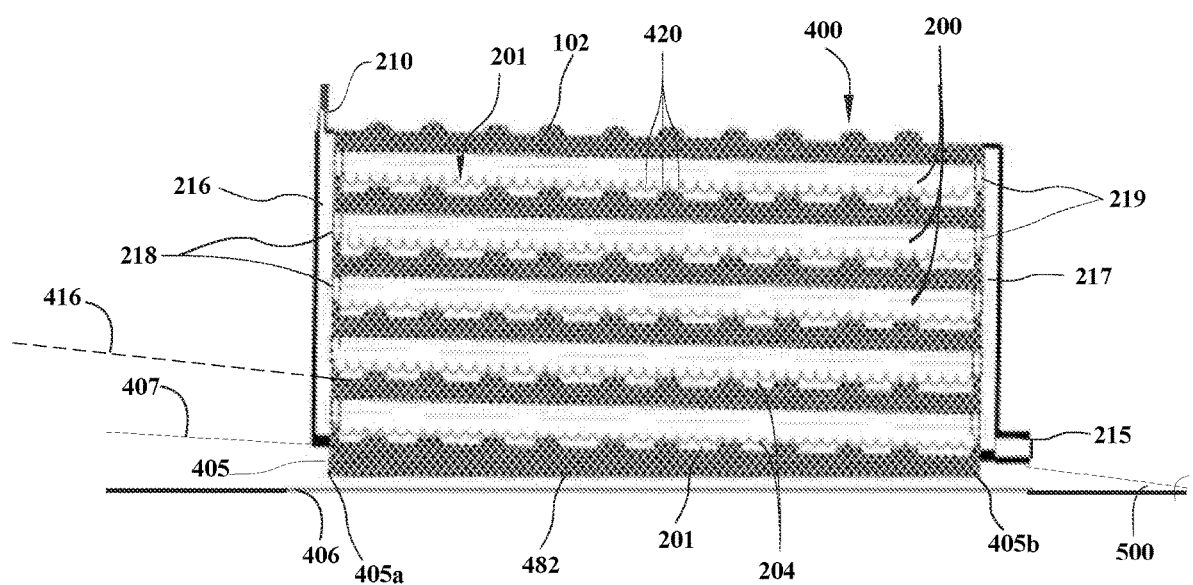
FIG. 3 is a schematic cross-section of a multilayer cell culture vessel in an embodiment of the present disclosure.

FIG. 3 is a schematic cross-section of a multilayer cell culture vessel 400 in an embodiment of the present disclosure. FIG. 3 illustrates an inlet 210 at the top of the vessel along one side of the vessel and an outlet 215 at the bottom of the vessel along another side of the vessel. In embodiments, the outlet 215 is on the opposite side of the vessel from the inlet 210. Inlet 210 is in fluid communication with each cell culture chamber 200 through an inlet manifold 21. Outlet 216 is in fluid communication with each cell culture chamber 200 through an outlet manifold 217. Each cell culture chamber has an inlet opening 218 between the cell culture chamber 200 and the inlet manifold 216 and an outlet opening 219 between the cell culture chamber 200 and the outlet manifold 217. In embodiments, and as shown in FIG. 3, no pump is necessary to flow liquid through the vessel and fluid flows by the force of gravity, flowing across the bottom surface of a cell culture chamber that is at an angle compared to a table plane 406.

Referring back to FIG. 2, liquid (such as media) can flow into the inlet 210, through the inlet manifold 216, into each cell culture chamber 200 through the inlet opening 218, out of the cell culture chamber 200 through the outlet opening 219, through the outlet manifold 217, and exit the vessel through the outlet 215. In embodiments, the flow of liquid may be accomplished by means of a pump 209, or by gravity. In embodiments, a liquid reservoir is provided both to provide liquid to the inlet 210 (213) and to collect liquid from the outlet 215 (211). In embodiments, a valve 212 may be present to control flow from a fresh media reservoir 213 and to a waste or collection reservoir 211. In embodiments, tubing may connect inlet to a pump (not shown) to allow liquid to be pumped into the inlet 210.

In embodiments, liquid can fill the vessel 400 from the outlet 215. For example, liquid can enter the outlet 215, by being pumped into the vessel 400 by the pump 209. When filling the vessel 400 in this way, liquid can enter the vessel through the inlet, and flow into the outlet manifold 217, can enter each cell culture chamber 200 through the outlet openings 219, fill each cell culture chamber 200, then fill the inlet manifold through the inlet openings 218. This allows air to exit the vessel through the inlet 210 as the vessel is filling. Filling the device in this manner may assist with evacuation of air out of the vessel and reduce the formation of bubbles during the filling process.

FIG. 3 also illustrates a multilayer cell culture vessel having internal tracheal spaces 204 adjacent to the bottom 201 of each cell culture chamber 200. In embodiments, the bottom 201 of each cell culture chamber is made from gas permeable, liquid impermeable material. Using this material increases gas exchange from the tracheal or gas spaces 220 through the gas permeable liquid impermeable material into the microcavities 420 which contain spheroids. This gas permeable material makes the vessel more versatile. For example, if used in a non-perfusion mode, cells have access to oxygen in the absence of perfused media. However, if the perfusion system is in operation, oxygen can be delivered to the cells dissolved in the circulating media. In this way, the vessel can be used both as a perfusion system and as a static system. However, in a perfusion system, this gas permeable material may not be necessary as oxygen is provided to the spheroids via the oxygenated media circulating through the cell culture chambers 200.

As shown in FIG. 3, the vessel has a base 405 that is angled. That is, the base 405 is thicker at the inlet side of the vessel 405a than at the outlet side of the vessel 405b. Because the base is thicker at the inlet side 405a than the outlet side 405b, the plane of the base (the base plane 407) is different from the plane of a table 406. The table plane 406 is intended to be a parallel to a plane perpendicular to gravity representing a table top or incubator shelf. The table plane 406 is parallel to the surface upon which the vessel 400 rests. The stacked cell culture chambers 200 are stacked on the base 405 and are parallel to the base plane 407. Therefore, each of the stacked cell culture chambers 200 are at an angle (see 417i of FIG. 5, for example) compared to the table plane 406.

Figure 4:
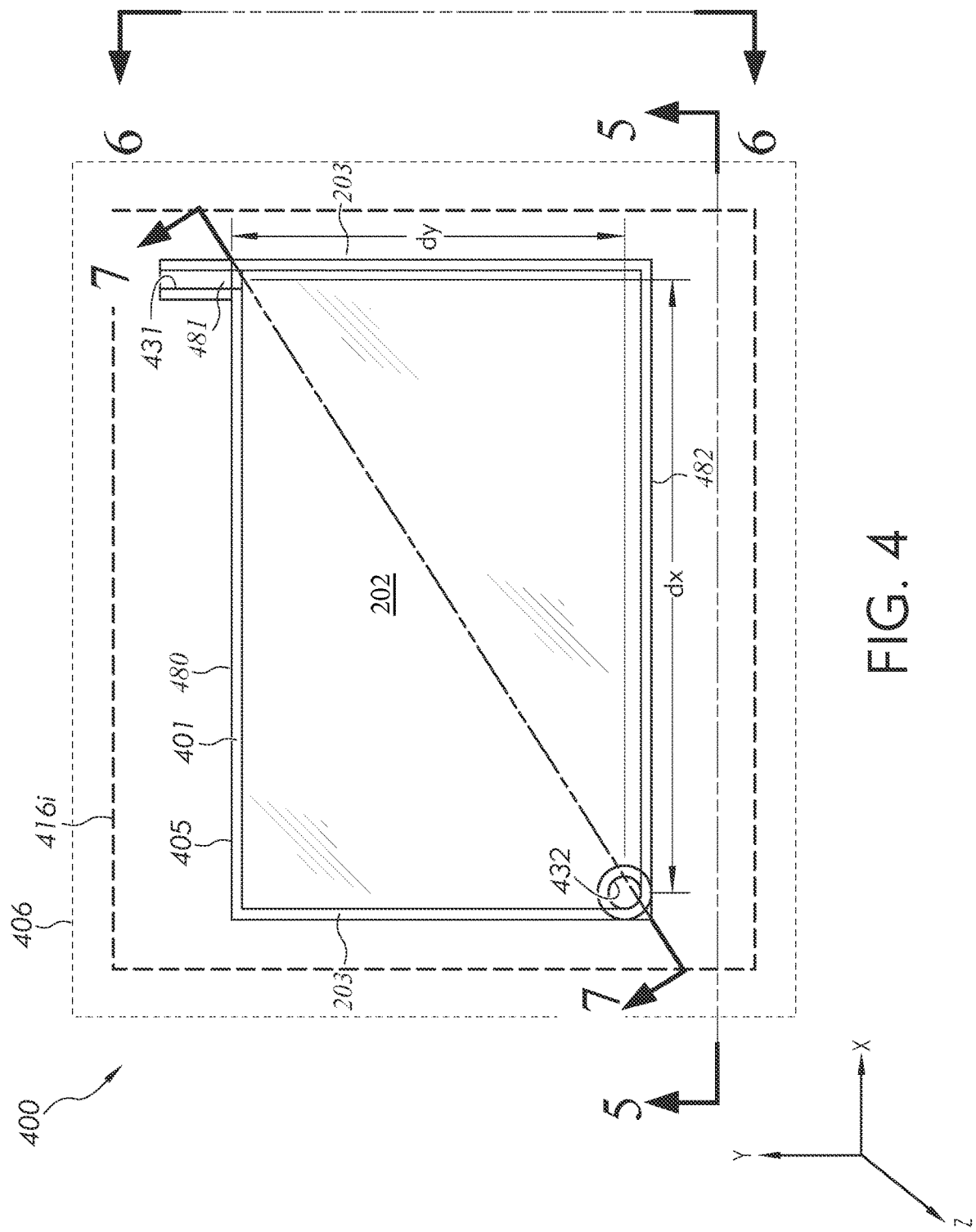
FIG. 4 schematically illustrates a plan view of an embodiment of a cell culture vessel including a base plane and a table plane in accordance with embodiments of the disclosure.
Figure 5:
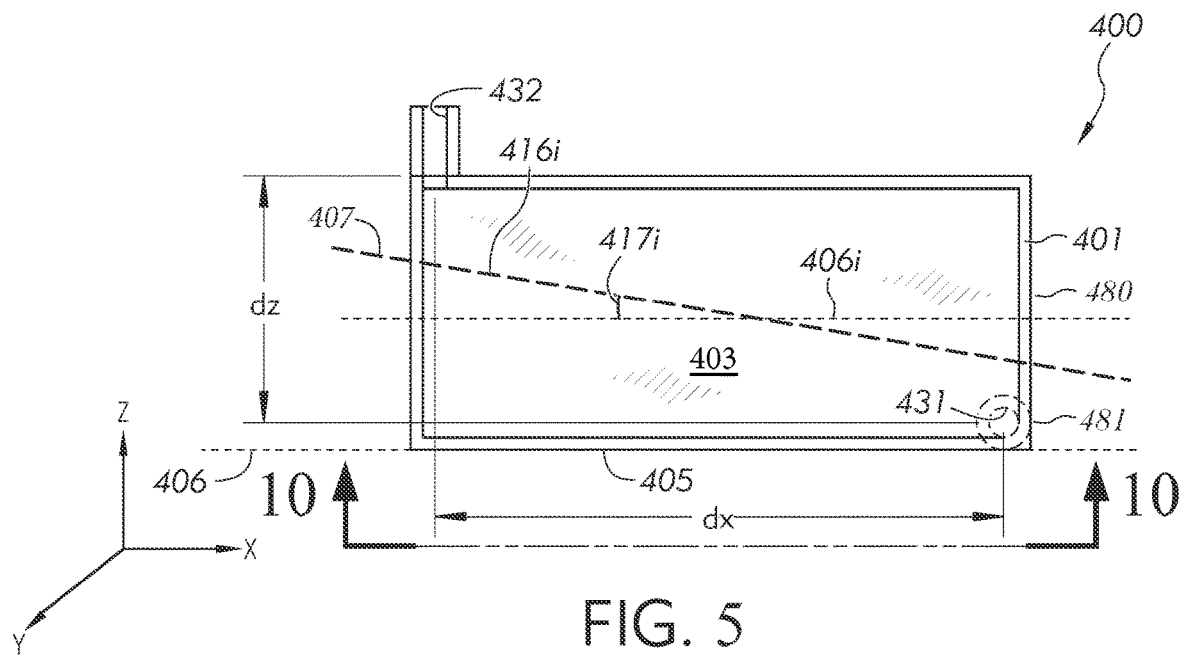
FIG. 5 shows a front view of an embodiment of the cell culture vessel including a base plane and a table plane along line 5-5 of FIG. 4 in accordance with embodiments of the disclosure.

In addition, if the cell culture vessel 400 is square or rectangular, the inlet may be on diagonal corners of the vessel (as shown in FIG. 5, for example). In that case, it may be that the base 405 has an angle along one plane of the vessel 400, or the base 405 may have an angle along two planes of the vessel 400. That is, the base may have an angle along an "X" axis (an X-Z angle, see, for example, 417i of FIG. 5), along a "Y" axis (a Y-Z axis, see, for example, angle 418i of FIG. 6), or along both an "X" and a "Y" axis. That is, the cell culture chambers may be oriented to direct liquid to the outlet wall 480 of the vessel 400 (see FIG. 5) or the cell culture chambers may be oriented to direct liquid to the outlet corner 481 of the vessel (see, for example, FIG. 4). Or, stated another way, an absolute value of at least one of the first angle and the second angle is greater than zero.

The base 405 defines a base plane 407 extending in a first direction "X" and a second direction "Y" perpendicular to the first direction. Each bottom surface 201 of each cell culture chamber 200 is parallel to the base plane 407. In embodiments, the bottom surface 201 of each cell culture chamber 200 is at a first angle relative to the first direction "X" (see 417i of FIG. 5) of the base plane 405 and a second angle relative to the second direction "Y" (see 418i of FIG. 6) of the table plane; and an absolute value of at least one of the first angle and the second angle is greater than zero. As FIG. 3 is a cross-sectional drawing, the second angle is not shown in FIG. 3, but see FIGS. 4-18 below.

A three-dimensional Cartesian coordinate system, including a first direction "X", a second direction "Y", and a third direction "Z" (with each direction being perpendicular to the other) is provided in FIGS. 3-18 to indicate a particular spatial orientation of the vessel 400 relative to the first direction "X", the second direction "Y", and the third direction "Z". Unless otherwise noted, it is to be understood, however, that the particular spatial orientation of the vessel 400 illustrated in the drawings figures provides an exemplary orientation that is not intended to limit the scope of the features of the vessel 400. Therefore, in some embodiments, one or more features of the vessel 400 can be provided at a different orientation than the particular orientation depicted in the drawings figures, without departing from the scope of the disclosure. In general, the third direction "Z" indicates the direction parallel with the direction of gravity.

Figure 6:
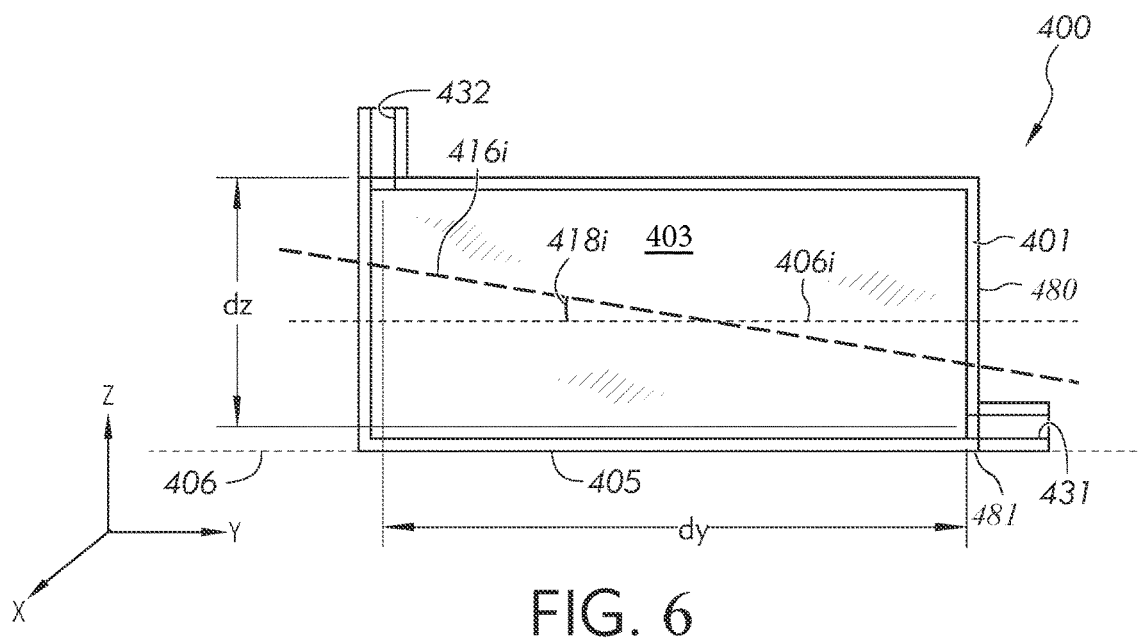
FIG. 6 shows a side view of an embodiment of the cell culture vessel including a base plane and a table plane along line 506 of FIG. 4 in accordance with embodiments of the disclosure.

For example, FIG. 4 schematically illustrates a plan view (top down) of an embodiment of the cell culture vessel 400, FIG. 5 shows a front view of the vessel 400 along line 5-5 of FIG. 4, and FIG. 6 shows a side view of the vessel 400 along line 6-6 of FIG. 4. In the drawing figures, the vessel 400 is illustrated as being manufactured from a clear (e.g., transparent) material; although, in some embodiments, the vessel 400 can, alternatively, be manufactured from one or more of a semi-transparent, semi-opaque, or opaque material without departing from the scope of the disclosure. While the embodiments shown in FIGS. 4-18 illustrate a single layer cell culture vessel, for ease of illustration. However, it is to be understood that the device can be in a multilayer configuration, as shown in FIG. 2 and FIG. 3. In the embodiments shown in FIGS. 4-18, the vessel wall 401 forms the bottom 482, top 202, and sidewalls 203 of the vessel.

As shown in FIG. 4, in some embodiments, the cell culture vessel 400 can include a base 405 having a bottom surface 482 parallel with a table plane 406 extending in the first direction "X" and the second direction "Y", where the first direction "X" and the second direction "Y" are perpendicular. Additionally, the vessel 400 can include a first aperture 432 (shown as inlet 210 in FIG. 2) or second aperture 431 (shown at the top of FIG. 4—FIG. 4 is a top-down view—and shown as outlet 215 in FIG. 2) extending through the wall 401 in fluid communication with the cell culture chamber 403, and a second aperture, or inlet 432 extending through the wall in fluid communication with the cell culture chamber 403. FIG. 4 illustrates shows the vessel having a top 202 and sidewalls 203. The sidewall from which the second aperture 431 extends is the outlet side 480 of the vessel 400. The corner from which the second aperture 431 extends is the outlet corner 481 of the vessel.

As shown in FIG. 5 and FIG. 6, in some embodiments, the second aperture 432 can be spaced from the first aperture 431 along an outward direction (e.g., the third direction "Z") extending away from the table plane 406 and perpendicular to the table plane 406, as represented by dimension "dz". Additionally, as shown in FIG. 4 and FIG. 5, in some embodiments, the first aperture 431 can be spaced from the second aperture 432 in the first direction "X", as represented by dimension "dx". Likewise, as shown in FIG. 4 and FIG. 6, in some embodiments, the first aperture 431 can be spaced from the second aperture 432 in the second direction "Y", as represented by dimension "dy". Note the Cartesian coordinates in the figures to assist with this description. In embodiments, the first aperture 431 and second aperture 432 inlet and outlet are on opposite walls of the vessel 400. The wall from which the first aperture 431 (the outlet) extends is the outlet wall 480. The corner containing the first aperture 431 (the outlet) is the outlet corner 481. FIGS. 5 and 6 show the vessel having a top 202, sidewalls 203 and a bottom 405 defining a cell culture chamber 403.

Figure 7:
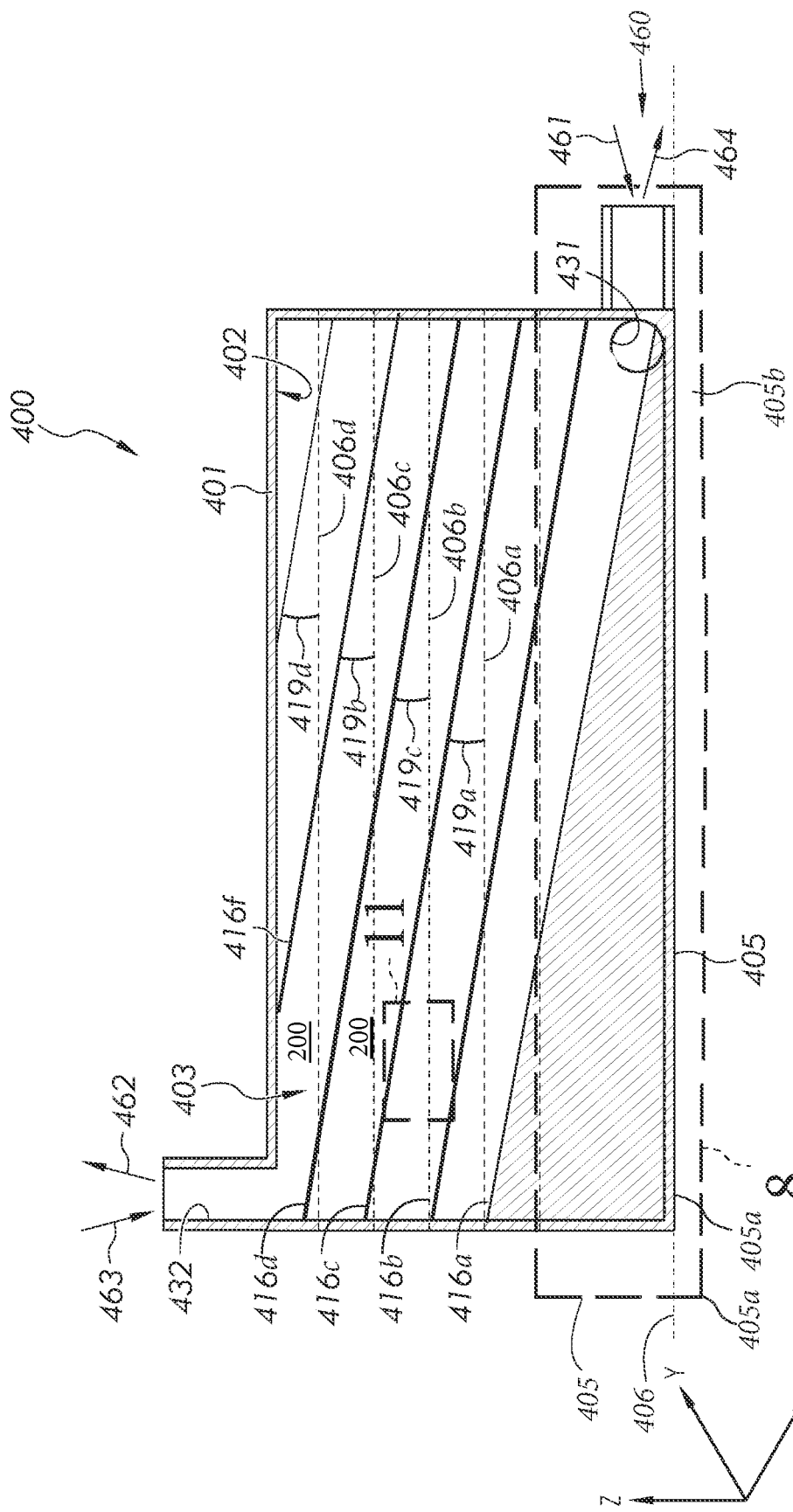
FIG. 7 shows an exemplary embodiment of a cross-sectional view of the cell culture vessel including a base plane and a table plane along line 7-7 of FIG. 4 in accordance with embodiments of the disclosure.
Figure 10:
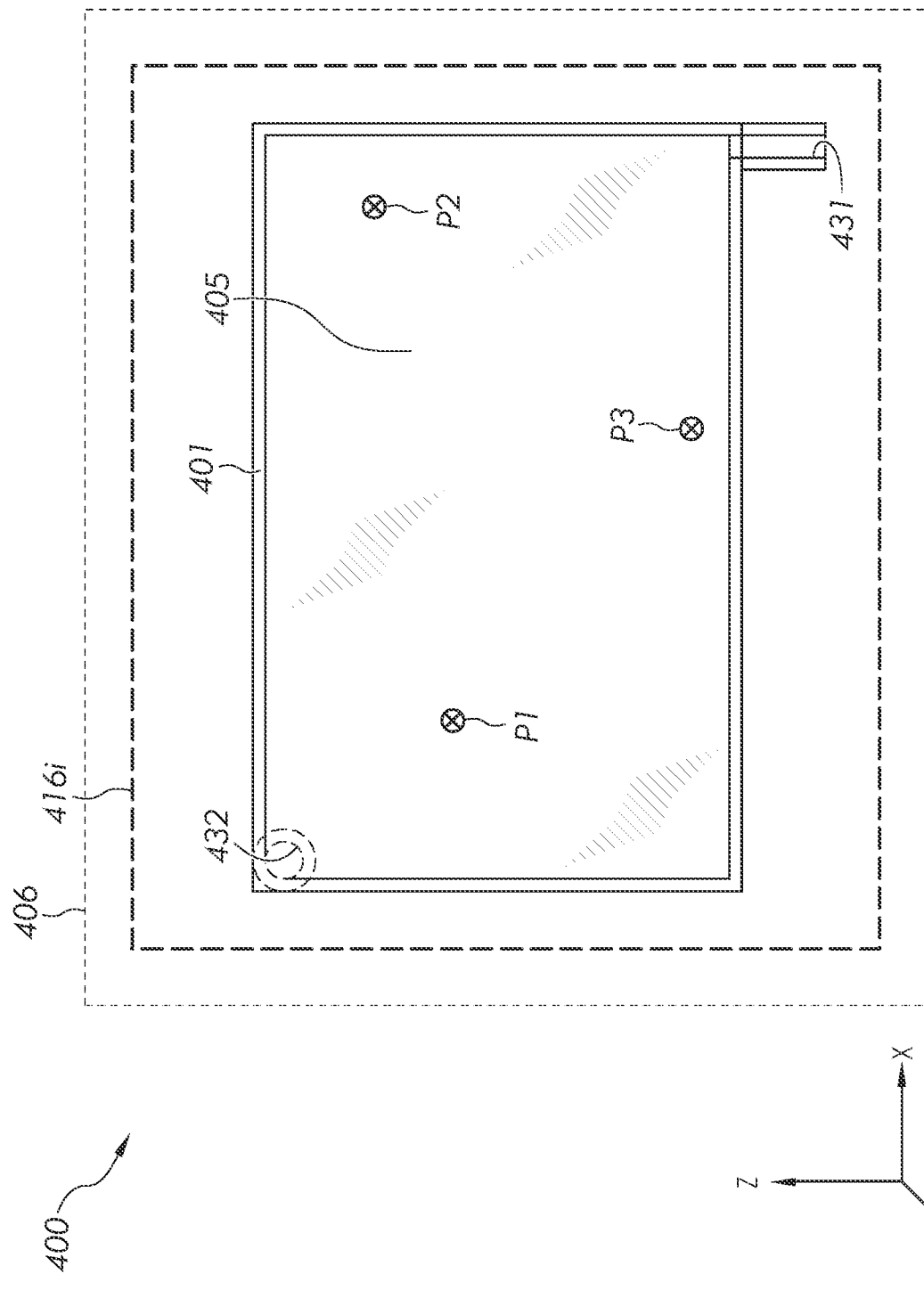
FIG. 10 shows a bottom view of the cell culture vessel including a base plane and a table plane along line 10-10 of FIG. 5 in accordance with embodiments of the disclosure.
Figure 11:
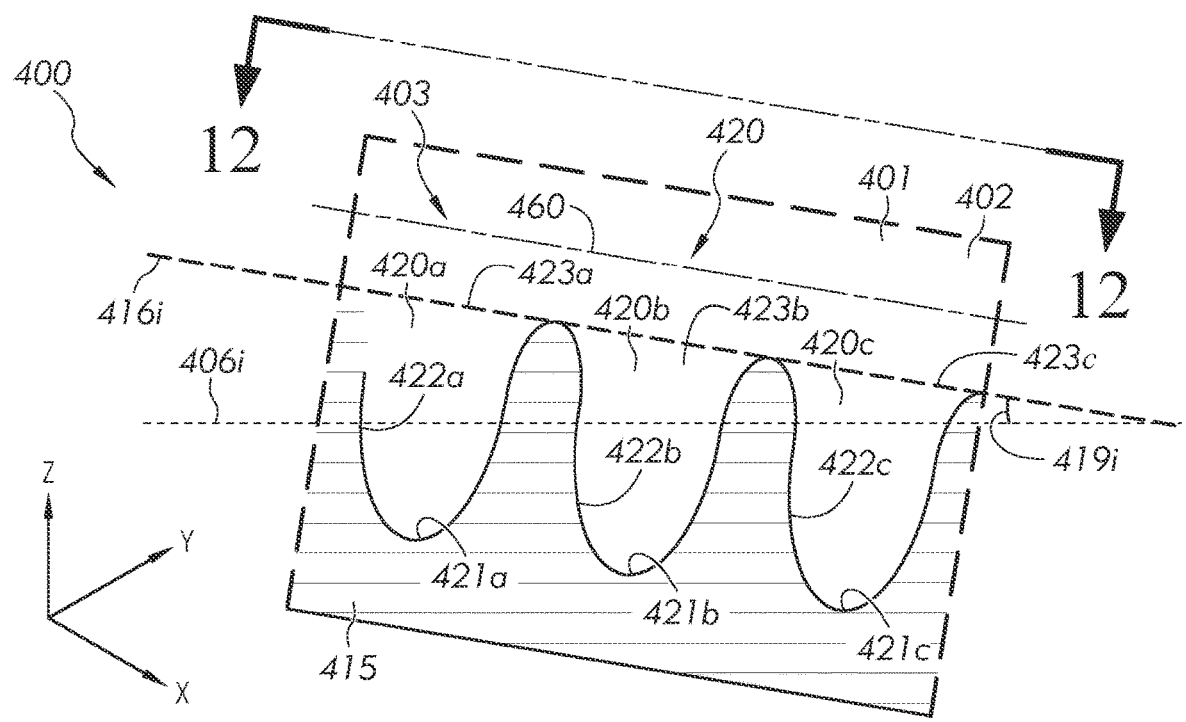
FIG. 11 illustrates an enlarged schematic representation of an exemplary embodiment of a portion of the cell culture vessel taken at view 55 of FIG. 7 including a substrate including a plurality of cell culture chambers in accordance with embodiments of the disclosure.
Figure 12:
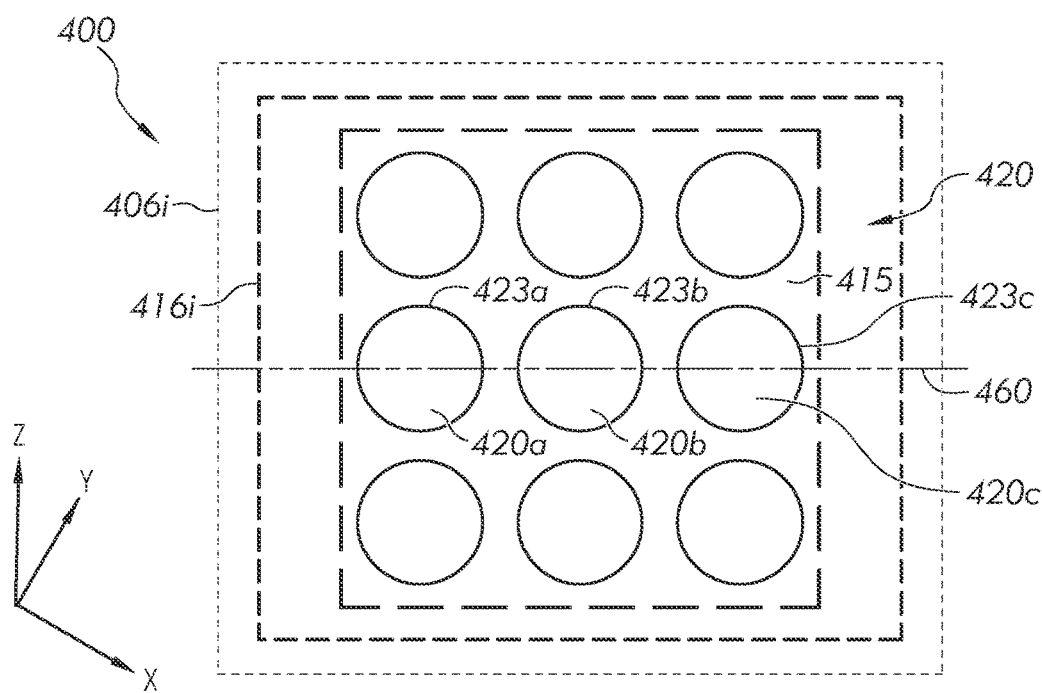
FIG. 12 shows a plan view of the portion of the cell culture vessel including a cell culture surface including the plurality of microcavities along line 12-12 of FIG. 11 in accordance with embodiments of the disclosure.

As shown in FIG. 11, which shows an enlarged view taken at view 11 of FIG. 7, and as shown in FIG. 12, which shows a partial view along line 12-12 of FIG. 11, in some embodiments, the vessel 400 can include an array of microcavities 420 in the bottom surface or substrate 415 of the cell culture chamber 403. In some embodiments, the microcavities 420 are formed in a substrate 415 that is placed into or attached to the cell culture chamber. In other embodiments, the microcavities 420 are formed directly into the bottom surface of the cell culture chamber or multiple chambers. Whether formed in a substrate or directly in the bottom surface of the cell culture chamber(s), the bottom surface 415 of the cell culture chamber can include a plurality of microcavities 420, and each microcavity 420a, 420b, 420c of the plurality of microcavities 420 can include a bottom rounded concave surface 421a, 421b, 421c defining the well of the microcavities 422a, 422b, 422c and an opening 423a, 423b, 423c defining a path into the well 422a, 422b, 422c. The bottom surface of the cell culture chamber or substrate 415 can define a substrate plane 416i, parallel with the base plane 407, and at an angle with respect to the table plane 406*i*, on which the opening 423*a*, 423*b*, 423*c* of each microcavity 420*a*, 420*b*, 420*c* of the plurality of microcavities 420 is located. For clarity purposes, the substrate 415 is not shown in, for example, FIGS. 4-18. Rather, the substrate plane 416*i*, parallel with the base plane 407, and at an angle with respect to the table plane 406*i*, is schematically illustrated in FIGS. 4-18 with the understanding that the bottom surface of the cell culture chamber, or substrate plane 416*i*, represents a plane on which the opening 423*a*, 423*b*, 423*c* of each microcavity 420*a*, 420*b*, 420*c* of the plurality of microcavities 420 of the substrate 415 is located, schematically represents the existence of the cell culture surface, or substrate 415 in the cell culture chamber 403.

As shown in FIG. 7, in some embodiments, the vessel 400 can include a plurality of cell culture chambers 200, defining a corresponding plurality of substrate planes 416*a*, 416*b*, 416*c*, 416*d*. Although four substrate planes 416*a*, 416*b*, 416*c*, 416*d* are provided, it is to be understood that, in some embodiments, one substrate plane (e.g., substrate plane 416*i*) can be provided, or more than one (e.g., two, three . . . seven, eight, ten, etc.) substrate planes can be provided without departing from the scope of the disclosure. Likewise, for clarity purposes, relative to the substrate planes 416*a*, 416*b*, 416*c*, 416*d*, a corresponding plurality of table planes 406*a*, 406*b*, 406*c*, 406*d*, are shown to schematically provide an illustrative representation of an orientation of the substrate planes 416*a*, 416*b*, 416*c*, 416*d* relative to the table plane 406. That is, in some embodiments, each of the substrate planes 416*a*, 416*b*, 416*c*, 416*d*, can intersect the table plane 406. Thus, the corresponding table planes 406*a*, 406*b*, 406*c*, 406*d*, which are parallel to the table plane 406, provide a schematic illustration of the orientation of each substrate plane 416*a*, 416*b*, 416*c*, 416*d*, relative to the table plane 406. Thus, in some embodiments, substrate plane 416*i* is shown with the understanding that the substrate plane 416*i* can be representative of and include features of any one or more of the plurality of substrate planes 416*a*, 416*b*, 416*c*, 416*d*, the substrate being the cell culture surface having an array of microcavities. Likewise, in some embodiments, table plane 406*i* is shown with the understanding that the table plane 406*i* can be representative of a corresponding plane parallel to the table plane 406 provided for purposes of clarity to schematically illustrate a respective orientation of the substrate plane 416*i* relative to the table plane 406.

Moreover, in some embodiments, a respective first angle 417*i* (on the "XY" plane), a respective second angle 418*i* (the "YZ" plane), and a respective plane angle 419*i* (which may include a first angle 417*i*, a second angle 418*i* or both) can be provided to an orientation of the base plane or substrate plane 416*i* relative to the table plane 406, as represented by a corresponding table plane 406*i*. For example, as shown in FIG. 5, in some embodiments, the base plane 416*i* can be oriented at a first angle 417*i* relative to the first direction "X". Likewise, as shown in FIG. 6, in some embodiments, the base plane 416*i* can be oriented at a second angle 418*i* relative to the second direction "Y". In some embodiments, an absolute value of at least one of the first angle 417*i* and the second angle 418*i* can be greater than zero. For example, in some embodiments an absolute value of the first angle 417*i* can be greater than zero, and an absolute value of the second angle 418*i* can be greater than zero. As shown in FIG. 7, in some embodiments, an absolute value of a base plane angle 419*a*, 419*b*, 419*c*, 419*d* between the table plane 406*a*, 406*b*, 406*c*, 406*d* and the substrate plane 416*a*, 416*b*, 416*c*, 416*d* can be from about 1° to about 30°. For example, in some embodiments, based at least on the orientation of the base plane 416*i* relative to the table plane 406 (e.g., relative to the first direction "X" defining the first angle 417*i*, and relative to the second direction "Y" defining the second angle 418*i*) an absolute value of the plane angle 419*a*, 419*b*, 419*c*, 419*d* can be from about 1° to about 30°. For example, in some embodiments, an absolute value of the plane angle 419*a*, 419*b*, 419*c*, 419*d* can be about 5°.

FIG. 8 and FIG. 9 show exemplary embodiments of a partial cross-section view of a vessel 400 taken at view 8 of FIG. 7. For example, as shown in FIG. 8, in some embodiments, the base 405 defining the base plane 407 can include a thicker portion 405*a* of the base 405 relative to a thinner portion 405*b* of the base 405. In addition or alternatively, as shown in FIG. 9, in some embodiments, the vessel 400 can include a step 405*c* positioned relative to the base 405 to elevate at least a portion of the vessel 400. The step 405*c* and the base 405 can define the base plane 407. For example, in some embodiments, a step 405*c* can be positioned underneath a corner of the base 405 to elevate the vessel 400 and provide the base 405 of the vessel 400 at an angle relative to a horizontal plane perpendicular to the direction of gravity.

In addition or alternatively, as shown in FIG. 10, which shows a bottom view of the vessel 400 along line 10-10 of FIG. 5, in some embodiments, the table plane 406 can be defined based on three points P1, P2, P3 located on the bottom side of base 405 of the vessel 400. For example, by selecting (e.g., identifying) three points P1, P2, P3 on the bottom side of the base 405, a plane, representing the table plane 406, can be defined. In some embodiments, one or more of the points P1, P2, P3 can include one or more structural features of the base 405, including but not limited to protrusions and bases that can be attached (e.g., integral, bonded) to the base 405 or separate from the base 405.

Turning back to FIG. 8, in some embodiments, the inner surface 402*a* of the base 405 can include an inclined surface 402*a* extending from the thicker portion 405*a* to the thinner portion 405*b*. In some embodiments, the inclined surface 402*a* can be parallel to the table plane 416*i*. Likewise, as shown in FIG. 9, in some embodiments, based at least on the elevation of a portion of the vessel 400, the step 405*c* can orient the inner surface 402 of the base 405 to include an inclined surface 402*a*. In some embodiments, the inclined surface 402*a* can be parallel to the table plane 416*i*. In some embodiments, the first aperture 431 can be positioned at a lower elevation relative to the direction of gravity than the second aperture 432. Thus, in some embodiments, based at least on the force of gravity, liquid within the cell culture chamber 403 can naturally drain toward the first aperture 431. Additionally, in some embodiments, the inclined surface 402*a* of the inner surface 402 of the wall 401 can cause the liquid to naturally drain toward the first aperture 431. In some embodiments, draining the liquid toward the first aperture 431 and out of the vessel 400 can aid in cleaning the cell culture chamber 403, prior to or after culturing cells in the vessel 400.

Figure 13:
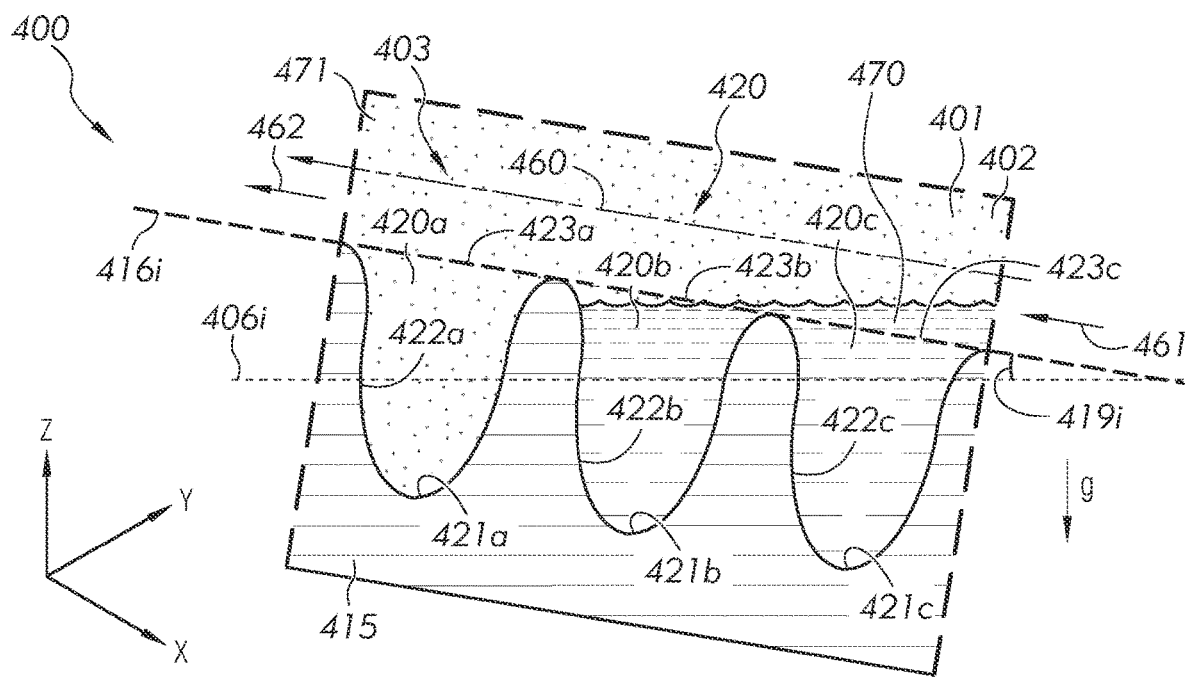
FIG. 13 shows an alternative exemplary embodiment of the portion of the cell culture vessel of FIG. 11 including a method of flowing a liquid along a flow path in accordance with embodiments of the disclosure.
Figure 14:
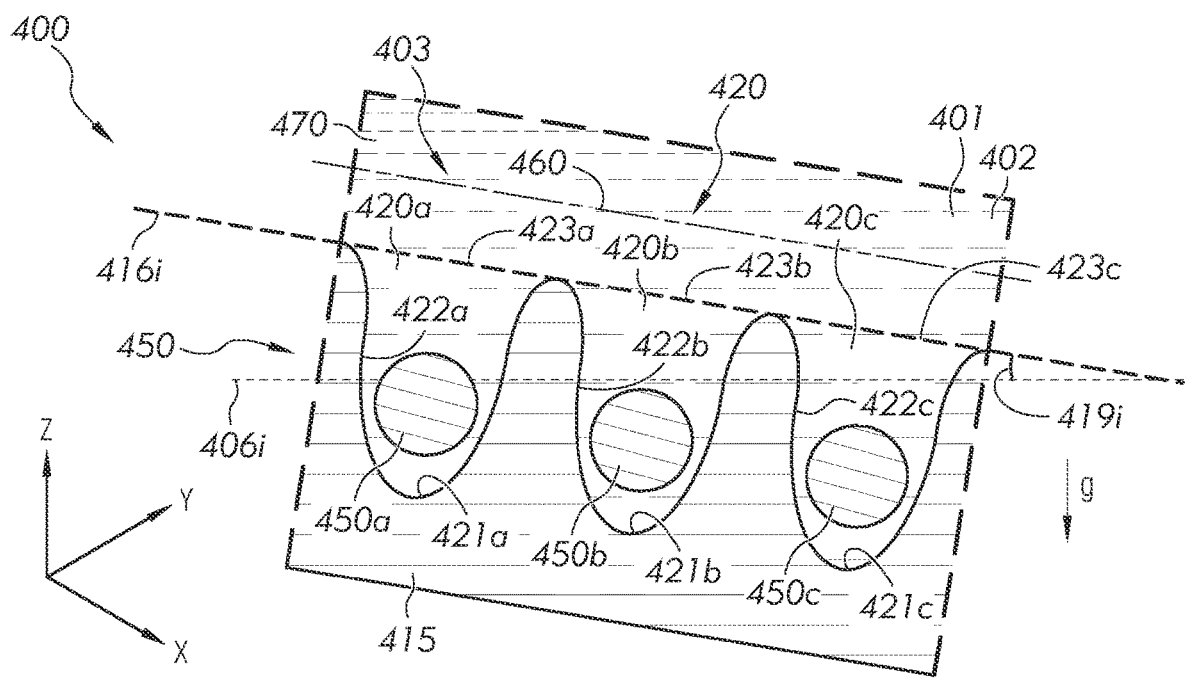
FIG. 14 shows an alternative exemplary embodiment of the portion of the cell culture vessel of FIG. 11 including a method of culturing cells in at least one microcavity of a plurality of microcavities in a bottom surface of a cell culture chamber in accordance with embodiments of the disclosure.

FIGS. 11-18 show exemplary embodiments of the portion of the vessel 400 including the substrate 415 of FIG. 11 with respect to methods of culturing cells in the cell culture vessel 400. For example, in some embodiments, as shown in FIG. 13, the method can include depositing liquid 470 in at least one microcavity 420*a*, 420*b*, 420*c* of the plurality of microcavities 420. As shown in FIG. 14, in some embodiments, the method can include culturing cells 450 (e.g., spheroid 450*a*, spheroid 450*b*, spheroid 450*c*) in microcavities 420*a*, 420*b*, 420*c* after depositing the liquid 470 in the microcavities 420a, 420b, 420c. In some embodiments, the table plane 406 (e.g., 406i) can be perpendicular relative to the direction of gravity "g" while culturing the cells 450 in the at least one microcavity 420a, 420b, 420c.

Additionally, in some embodiments, the method can include flowing material in a flow direction 460 parallel to the substrate plane 416i while culturing the cells 450 in the at least one microcavity 420a, 420b, 420c. For example, as shown in FIG. 7, in some embodiments, as represented by arrow 461, the method can include passing liquid 470 through the first aperture 431 from outside the vessel 400 into the cell culture chamber 403, and (as shown in FIG. 13, by the arrow 461) flowing the liquid 470 in the cell culture chamber 403 along the flow direction 460 parallel to the substrate plane 416i. Likewise, in some embodiments, as shown by arrow 462 in FIG. 13, the method can include passing gas 471 through the second aperture 432 (as shown in FIG. 7, by the arrow 462) from the cell culture chamber 403 to outside the vessel 400 while flowing the liquid 470 in the cell culture chamber 403 along the flow direction 460. In some embodiments, the method can include culturing cells 450 in at least one microcavity 420a, 420b, 420c of the plurality of microcavities 420 while flowing the liquid 470 in the cell culture chamber 403 along the flow direction 460. For example, in some embodiments, the method can include culturing cells 450 in at least one microcavity 420a, 420b, 420c while at least one of passing liquid 470 through the first aperture 431 from outside the vessel 400 into the cell culture chamber 403 (arrow 461) and passing gas 471 through the second aperture 432 from the cell culture chamber 403 to outside the vessel 400 (arrow 462).

Figure 15:
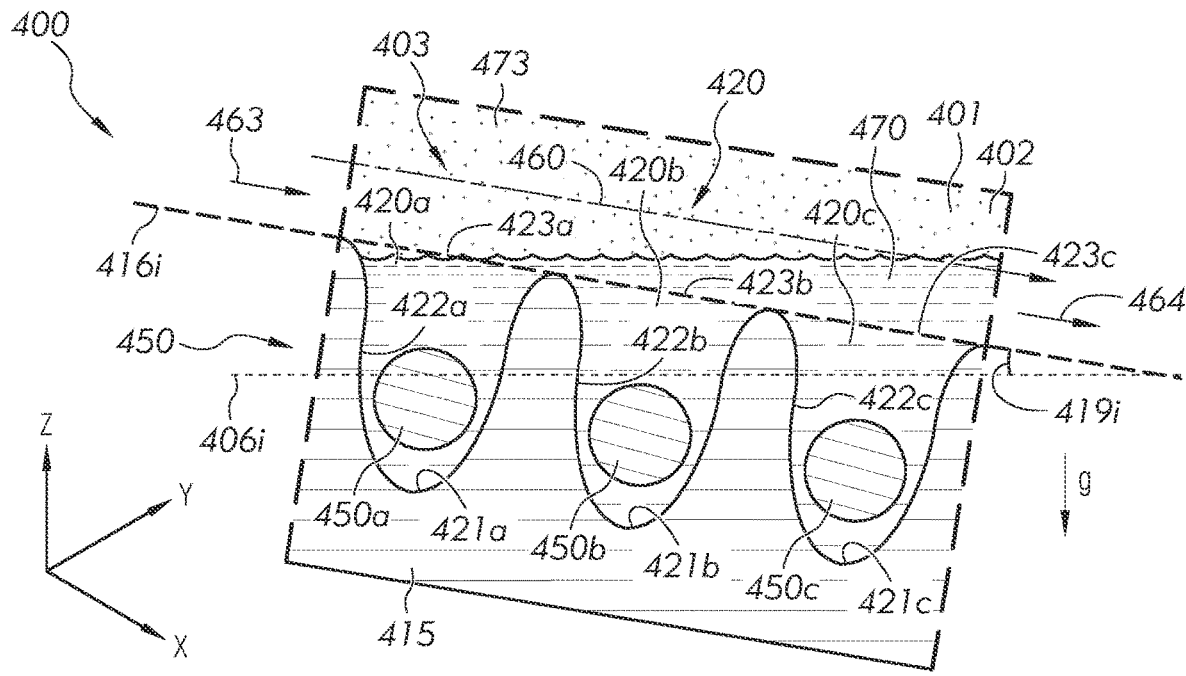
FIG. 15 shows an alternative exemplary embodiment of the portion of the cell culture vessel of FIG. 11 including a method of culturing cells in at least one microcavity of a plurality of microcavities in a bottom surface of a cell culture chamber while flowing a liquid and a gas along a flow path in accordance with embodiments of the disclosure.
Figure 16:
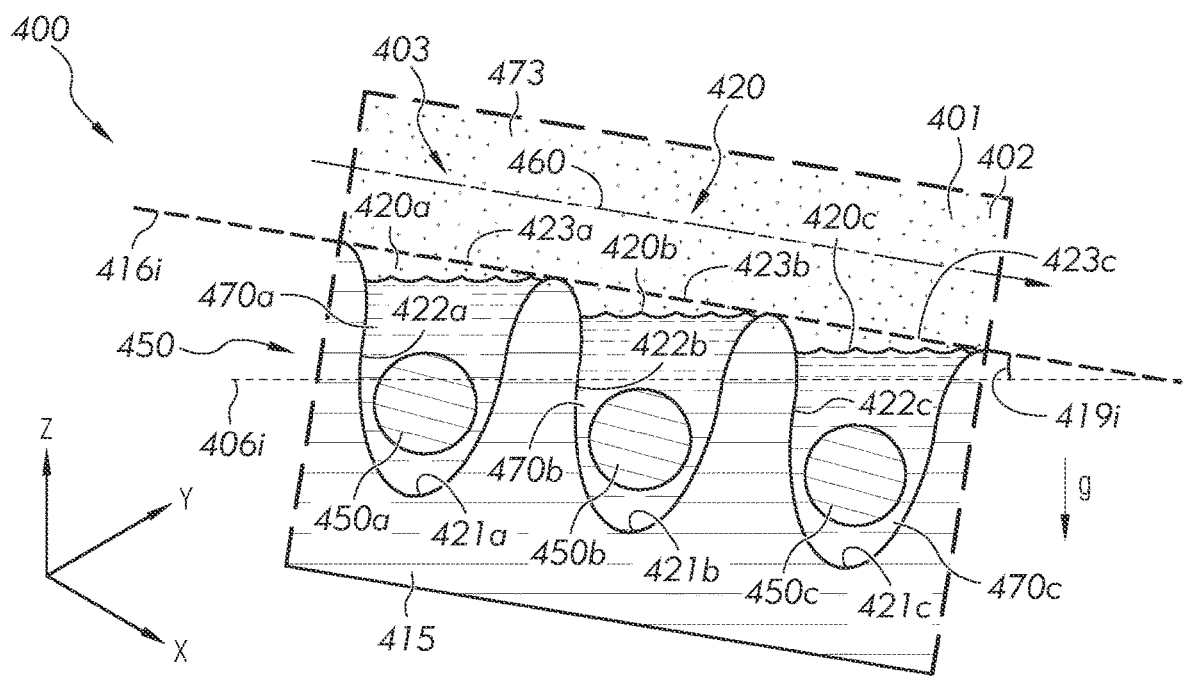
FIG. 16 shows an alternative exemplary embodiment of the portion of the cell culture vessel of FIG. 11 including a method of culturing cells in at least one microcavity of a plurality of microcavities of a bottom surface of a cell culture chamber in accordance with embodiments of the disclosure.

As shown in FIG. 15, in some embodiments, the method can include flowing the liquid 470 in the cell culture chamber 403 along the flow direction 460 parallel to the substrate plane 416i, and (as represented by arrow 464) passing the liquid 470 through the first aperture 431 from the cell culture chamber 403 to outside the vessel 400 (as shown in FIG. 7, by the arrow 464). Additionally, as shown by arrow 463 the method can include passing gas 473 through the second aperture 432 from outside the vessel 400 into the cell culture chamber 403 (as shown in FIG. 7, by arrow 463) while flowing the liquid 470 in the cell culture chamber 403 along the flow direction 460. As shown in FIG. 16, in some embodiments, the method can include culturing cells 450 in at least one microcavity 420a, 420b, 420c of the plurality of microcavities 420 while flowing the liquid 470 in the cell culture chamber 403 along the flow direction 460. In some embodiments, based at least on passing the gas 473 into the cell culture chamber 403 (arrow 463), the liquid 470 can be removed from the cell culture chamber 403 and, in some embodiments, each microcavity 420a, 420b, 420c can include a respective portion of liquid 470a, 470b, 470c. For example, in some embodiments, the method can include culturing cells 450 in at least one microcavity 420a, 420b, 420c while at least one of passing gas 473 through the second aperture 432 from outside the vessel 400 into the cell culture chamber 403 (arrow 463) and passing liquid 470 through the first aperture 431 from the cell culture chamber 403 to outside the vessel 400 (arrow 464).

Figure 17:
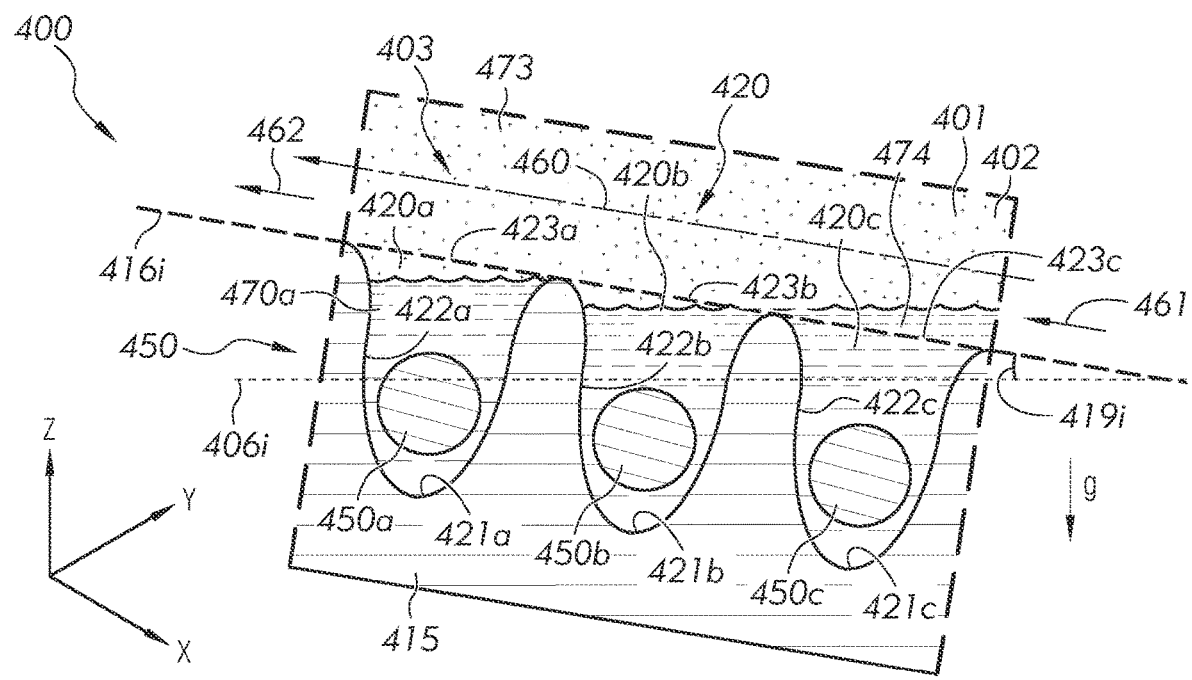
FIG. 17 shows an alternative exemplary embodiment of the portion of the cell culture vessel of FIG. 11 including a method of culturing cells in at least one microcavity of a plurality of microcavities of a substrate while flowing a liquid and a gas along a flow path in accordance with embodiments of the disclosure.
Figure 18:
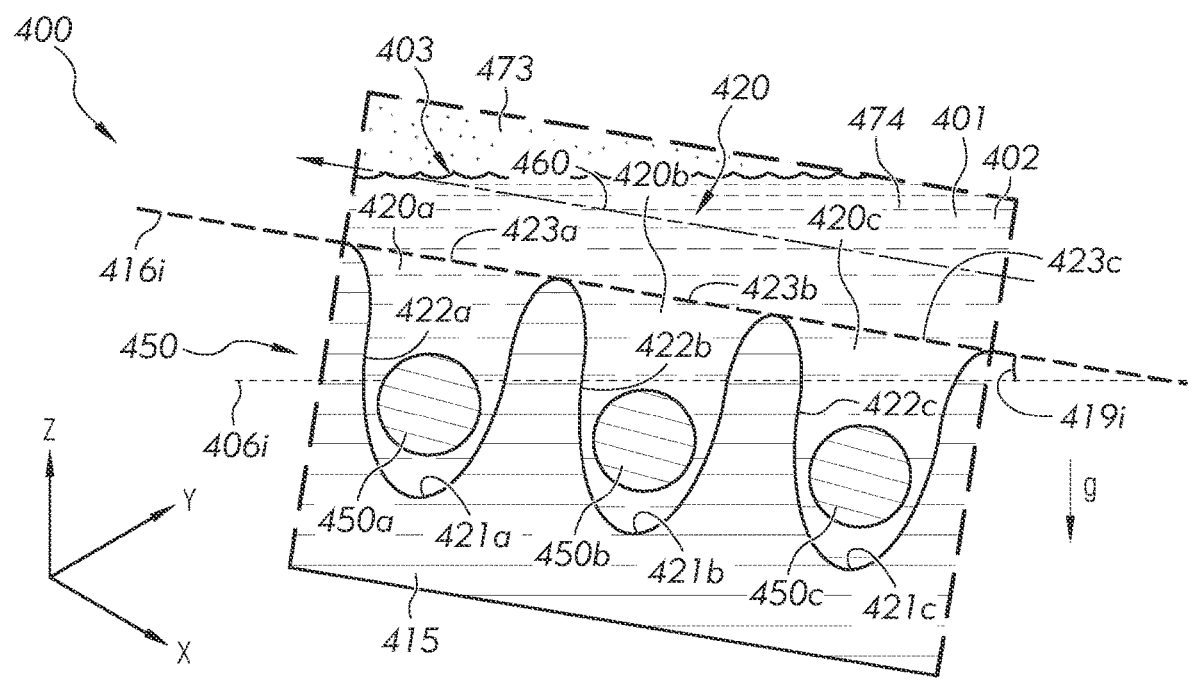
FIG. 18 shows an alternative exemplary embodiment of the portion of the cell culture vessel of FIG. 11 including a method of culturing cells in at least one microcavity of a plurality of microcavities of a substrate in accordance with embodiments of the disclosure.

As shown in FIG. 17 and FIG. 18, in some embodiments, the method can include flowing material in a flow direction 460 parallel to the substrate plane 416i while culturing the cells 450 in the at least one microcavity 420a, 420b, 420c. For example, as shown in FIG. 7, in some embodiments, as represented by arrow 461, the method can include passing liquid 474 (e.g., different liquid as compared to liquid 470) through the first aperture 431 from outside the vessel 400 into the cell culture chamber 403, and (as shown in FIG. 61, by the arrow 461) flowing the liquid 474 in the cell culture chamber 403 along the flow direction 460 parallel to the substrate plane 416i. In some embodiments, the liquid 474 can displace the liquid 470a, 470b, 470c in each microcavity 420a, 420b, 420c with, for example, new liquid 474 that aids in the culturing of the cells 450. Likewise, in some embodiments, as shown by arrow 462 in FIG. 17, the method can include passing gas 473 through the second aperture 432 (as shown in FIG. 7, by the arrow 462) from the cell culture chamber 403 to outside the vessel 400 while flowing the liquid 474 in the cell culture chamber 403 along the flow direction 460. In some embodiments, the method can include culturing cells 450 in at least one microcavity 420a, 420b, 420c of the plurality of microcavities 420 while flowing the liquid 474 in the cell culture chamber 403 along the flow direction 460. For example, in some embodiments, the method can include culturing cells 450 in at least one microcavity 420a, 420b, 420c while at least one of passing liquid 474 through the first aperture 431 from outside the vessel 400 into the cell culture chamber 403 (arrow 461) and passing gas 473 through the second aperture 432 from the cell culture chamber 403 to outside the vessel 400 (arrow 462).

In some embodiments, the passing of liquid and gas in to or out of the first aperture 431 and the second aperture 432 can be accomplished automatically based on, for example, operation of a system including pumps, reservoirs, tubing, etc. connected to at least one of the first aperture 431 and the second aperture 432 that facilitates automatic passing of liquid and gas into or out of the first aperture 431 and the second aperture 432. Accordingly, in some embodiments, for example during extended periods of culturing cells 450, media exchange (e.g., replacement, replenishment, removal) of material (e.g., nutrients and waste) can occur automatically based on operation of the system without, for example, human interaction. Likewise, media exchange can occur without physical manipulation of the vessel 400. For example, unlike other vessels that can be tilted, inverted, rotated, etc. to exchange media within the cell culture chamber 403 during culturing, the vessel 400 can remain stationary (e.g., without relative movement) during the entire cell culturing process and the media can, nonetheless be exchanged based on the features of the disclosure.

Moreover, providing the substrate plane 416i at an angle (e.g., first angle 417i, second angle 418i, plane angle 419i) relative to the table plane 406 can provide several advantages. For example, in some embodiments, providing the substrate 415 at an orientation with an absolute value of the plane angle 419i from about 1° to about 30° relative to the table plane 406 when, for example, the table plane 406 is substantially perpendicular relative to the direction of gravity "g" can provide the substrate 415 at an orientation that provides better culturing of the cells 450. For example, without intending to be bound by theory, it is believed that, in some embodiments, orienting the substrate plane 416i with an absolute value of the plane angle 419i less than 1° would be insufficient to accommodate the flow of liquid along the flow direction 460 without entrapping gas (e.g., air pockets) between two or more substrates 415 and/or within one or more microcavities 420a, 420b, 420c. Additionally, in some embodiments, in order to flow liquid along the flow direction 460 when the substrate plane 416i is oriented with an absolute value of the substrate plane angle 419i less than 1°, a velocity of the flow can be increased with negative effects on cells and negative effects on retention of cellular spheroids within the microcavities 420a, 420b, 420c. That is, if the substrate plane angle is less than 1°, less than 5°, or less than 30°, for example, the flow rate necessary to effect efficient replacement of media may create turbulence that might disrupt spheroids residing in microcavities. Thus, providing the substrate 415 at an orientation with an absolute value of the plane angle 419i from about 1° to about 30° relative to the table plane 406 can permit liquid to gradually enter each microcavity 420a, 420b, 420c thus reducing or preventing the likelihood of gas becoming entrapped within the microcavities 420a, 420b, 420c and reducing or preventing the likelihood of disrupting cells being cultured within the microcavities 420a, 420b, 420c.

That is, in some embodiments, based at least in part of the force of gravity, liquid can naturally flow along the substrate 415 while culturing cells 450 without dislodging or disturbing the culturing of the cells 450. Alternatively, orienting the substrate plane 416i with an absolute value of the plane angle 419i less than 1° could lessen the effect of the force of gravity to cause the liquid to naturally flow in the flow direction 460 along the substrate 415, in which case, an increased velocity flow that could dislodge or disturb the cells 450 can be employed. Likewise, in some embodiments, orienting the substrate plane 416i with an absolute value of the plane angle 419i greater than 30° could cause cells 450 within the microcavities 420a, 420b, 420c to fall out of the microcavities 420a, 420b, 420c (e.g., dislodge, dislocate) during culturing. Accordingly, in some embodiments, orienting the substrate plane 416i with an absolute value of the plane angle 419i from about 1° to about 30° (e.g., from about 5° to about 30°, from about 5° to about 25°, from about 5° to about 20°, from about 5° to about 15°, from about 5° to about 10°, from about 10° to about 20°, from about 10° to about 30°, from about 1° to about 10°, from about 1° to about 5°, about 3°, about 5°, about 7° can provide several advantages that cannot be obtained by cell culture vessels including substrates provided at different orientations outside the range of from about 1° to about 30°.

Throughout the disclosure, the terms "material", "liquid", and "gas" can be used to describe properties of a material employed when, for example, culturing cells in the cell culture vessel. Unless otherwise noted, for purposes of the disclosure, "material" can include fluid material (e.g., liquid or gas). Additionally, material can include a culture solution or media including a liquid including solid particles (e.g., cells) suspended in the liquid. Unless otherwise noted, for purposes of the disclosure, "liquid" can include cleaning or rinsing solutions, aqueous solutions, or other liquid that can be added to or removed from the vessel to, for example, clean the cell culture chamber, sterilize one or more features of the substrate and the vessel, prepare the substrate for cellular growth and other uses of liquid. Additionally, liquid can include a culture solution or media including a liquid including solid particles (e.g., cells) suspended in the liquid. Unless otherwise noted, for purposes of the disclosure, "gas" can include air, filtered or treated air, or other gases.

Throughout the disclosure, the terms "non-permeable", "gas-permeable", and "porous" can be used to describe properties (e.g., material properties, characteristics, parameters) of one or more features of a substrate.

Unless otherwise noted, for purposes of the disclosure, a "non-permeable" substrate (e.g., material of a non-permeable substrate) is considered to be impermeable to solid, liquid, and gas under normal conditions (e.g., no external influence including but not limited to pressure and force) and, therefore, does not permit the transfer of solid, liquid, or gas in to, through, or out of, the non-permeable substrate under normal conditions. In some embodiments, a non-permeable substrate can form a portion of the wall of the vessel. Additionally, the cell culture chamber of the vessel is considered to be sterile when a non-permeable substrate forms a portion of the wall of the vessel because bacteria, for example, cannot pass through the non-permeable substrate. However, when filling the plurality of microcavities of the substrate with material, gas can become trapped within the microcavity of a non-permeable substrate based on surface tension of the liquid, thereby, in some embodiments, preventing material from filling the microcavities and preventing growth of a spheroid.

Unless otherwise noted, for purposes of the disclosure, a "gas-permeable" substrate (e.g., material of a gas-permeable substrate) is considered to be impermeable to solid and liquid, and permeable to gas under normal conditions. Therefore, a gas-permeable substrate does not permit the transfer of solid and liquid in to, through, or out of, the gas-permeable substrate and does permit the transfer of gas in to, through, or out of, the gas-permeable substrate. In some embodiments, a gas-permeable substrate can form a portion of the wall of the vessel. Additionally, the cell culture chamber of the vessel is considered to be sterile when a gas-permeable substrate forms a portion of the wall of the vessel because bacteria, for example, cannot reasonably pass through the gas-permeable substrate. However, although the substrate is gas-permeable, gas can still become trapped in the microcavity during filling with material because gas-permeation rates through the gas-permeable substrate can be slower than the rate required to displace gas from the cavity under ordinary operating conditions and can therefore take an unacceptably long amount of time to permeate through the substrate. Thus, in some embodiments, slowly filling the microcavities allows the liquid front to enter each microcavity at an angle, thereby displacing gas as the liquid fills the microcavity. In some embodiments, after filling the cavity with liquid, gas can permeate (slowly) through the gas-permeable substrate.

Unless otherwise noted, for purposes of the disclosure, a "porous" substrate (e.g., material of a porous substrate) is considered to be impermeable to solid and permeable to liquid and gas under normal conditions. Therefore, a porous substrate does not permit the transfer of solid in to, through, or out of, the porous substrate and does permit the transfer of liquid and gas in to, through, or out of, the porous substrate. A porous substrate cannot form a portion of the vessel because bacteria can pass through a porous substrate, thus causing sterility issues in the cell culture chamber. Thus, when using a porous substrate, the substrate must be enclosed (entirely enclosed) in the sterile cell culture chamber of the vessel. During filling of the microcavities with material, however, gas can escape (e.g., pass) through the porous substrate. Thus, filling of the microcavities can be performed rapidly without concern for entrapping gas in the microcavities. In some embodiments, liquid can only pass through the porous substrate with added pressure or physical contact and disturbance of the substrate. Thus, in some embodiments, material including liquid can be contained in the microcavities of the substrate so long as the substrate is not exposed to added pressure or physical contact and disturbance. For example, in some embodiments, the porous substrate can be placed in the cell culture chamber to allow gas to pass through the substrate during filling as well as during culturing and to isolate the substrate from added pressure or physical contact and disturbance from external forces (e.g., outside the cell culture chamber).

A number of aspects of cell culture vessels and methods of culturing cells have been disclosed herein. A summary of some selected aspects is presented below.

In a first aspect, a cell culture vessel includes a base defining a base plane extending in a first direction and a second direction perpendicular to the first direction; a wall including an inner surface defining a cell culture chamber of the vessel; and a bottom surface of the cell culture chamber. The bottom surface of the cell culture chamber may be a separate substrate inserted into the cell culture chamber or may be a wall of the cell culture chamber. The substrate or bottom surface includes a plurality of microcavities, each microcavity of the plurality of microcavities includes a concave surface defining a well and an opening defining a path into the well. The substrate defines a substrate plane on which the opening of each microcavity of the plurality of microcavities is located, the substrate plane is oriented at a first angle relative to the first direction and at a second angle relative to the second direction, and an absolute value of at least one of the first angle and the second angle is greater than zero.

A second aspect is a cell culture vessel according to the first aspect, where an absolute value of the first angle is greater than zero, and an absolute value of the second angle is greater than zero.

A third aspect is a cell culture vessel according to aspect 1 or aspect 2, where an absolute value of a plane angle between the base plane and the substrate plane is from about 1° to about 30°.

A fourth aspect is a cell culture vessel according to aspect 3, where an absolute value of the plane angle is about 5°.

A fifth aspect is a cell culture vessel according to any one of aspects 1-4, including a first aperture extending through the wall in fluid communication with the cell culture chamber, and a second aperture extending through the wall in fluid communication with the cell culture chamber, where the second aperture is spaced from the first aperture along an outward direction extending away from the base plane and perpendicular to the base plane.

A sixth aspect is a cell culture vessel according to aspect 5, where the first aperture is spaced from the second aperture in the first direction.

A seventh aspect is a cell culture vessel according to aspect 5 or aspect 6, where the first aperture is spaced from the second aperture in the second direction.

In an eighth aspect, a method of culturing cells in the cell culture vessel of any one of aspects 1-7, includes depositing liquid in at least one microcavity of the plurality of microcavities, and culturing cells in the at least one microcavity after depositing the liquid in the at least one microcavity.

A ninth aspect is a method of culturing cells according to aspect 8, where the base plane is perpendicular relative to the direction of gravity while culturing the cells in the at least one microcavity.

A tenth aspect is a method of culturing cells according to aspect 8 or aspect 9, including flowing material in a flow direction parallel to the substrate plane while culturing the cells in the at least one microcavity.

In an eleventh aspect, a method of culturing cells in the cell culture vessel of any one of aspects 5-7 includes passing liquid through the first aperture from outside the vessel into the cell culture chamber, and flowing the liquid in the cell culture chamber along a flow direction parallel to the substrate plane.

A twelfth aspect is a method of culturing cells according to aspect 11, including passing gas through the second aperture from the cell culture chamber to outside the vessel while flowing the liquid in the cell culture chamber along the flow direction.

A thirteenth aspect is a method of culturing cells according to aspect 11 or aspect 12, including culturing cells in at least one microcavity of the plurality of microcavities while flowing the liquid in the cell culture chamber along the flow direction.

A fourteenth aspect is a method of culturing cells according to aspect 13, where the base plane is perpendicular relative to the direction of gravity while culturing the cells in the at least one microcavity.

In a fifteenth aspect, a method of culturing cells in the cell culture vessel of any one of aspects 5-7 includes flowing liquid in the cell culture chamber along a flow direction parallel to the substrate plane, and passing the liquid through the first aperture from the cell culture chamber to outside the vessel.

A sixteenth aspect is a method of culturing cells according to aspect 15, including passing gas through the second aperture from outside the vessel into the cell culture chamber while flowing the liquid in the cell culture chamber along the flow direction.

A seventeenth aspect is a method of culturing cells according to aspect 15 or aspect 16, including culturing cells in at least one microcavity of the plurality of microcavities while flowing the liquid in the cell culture chamber along the flow direction.

An eighteenth aspect is a method of culturing cells according to aspect 17, where the base plane is perpendicular relative to the direction of gravity while culturing the cells in the at least one microcavity.

In a nineteenth aspect, a method of culturing cells includes depositing liquid in at least one microcavity of a plurality of microcavities of a substrate positioned in a cell culture chamber of a vessel while a base plane of the vessel is oriented perpendicular relative to the direction of gravity, the base plane extending in a first direction and a second direction perpendicular to the first direction, where each microcavity of the plurality of microcavities includes a concave surface defining a well and an opening defining a path into the well, where the substrate defines a substrate plane on which the opening of each microcavity of the plurality of microcavities is located, where the substrate plane is oriented at a first angle relative to the first direction and at a second angle relative to the second direction, and an absolute value of at least one of the first angle and the second angle is greater than zero; culturing cells in the at least one microcavity after depositing the liquid in the at least one microcavity; and flowing material in a flow direction parallel to the substrate plane while culturing the cells in the at least one microcavity.

A twentieth aspect is a method of culturing cells according to aspect 19, where an absolute value of the first angle is greater than zero, and an absolute value of the second angle is greater than zero.

A twenty-first aspect is a method of culturing cells according to aspect 19 or aspect 20, where an absolute value of a plane angle between the base plane and the substrate plane is from about 1° to about 30°.

A twenty-second aspect is a method of culturing cells according to aspect 21, where an absolute value of the plane angle is about 5°.

A twenty-third aspect is a method of culturing cells according to any one of aspects 19-22, including passing liquid through a first aperture in a wall of the vessel from outside the vessel into the cell culture chamber and passing gas through a second aperture in the wall of the vessel from the cell culture chamber to outside the vessel.

A twenty-fourth aspect is a method of culturing cells according to aspect 23, including passing gas through the second aperture from outside the vessel into the cell culture chamber and passing liquid through the first aperture from the cell culture chamber to outside the vessel.

A twenty-fifth aspect is a method of culturing cells according to aspect 23 or aspect 24, where the first aperture is positioned at a lower elevation relative to the direction of gravity than the second aperture.

In a twenty-sixth aspect, a cell culture vessel includes a substrate including a plurality of microcavities; a wall, the substrate and an inner surface of the wall define a cell culture chamber of the vessel; an aperture extending through the wall in fluid communication with the cell culture chamber; a first portion of the inner surface positioned opposite the aperture along an axis of the vessel, the substrate spans a length of the cell culture chamber that extends along the axis of the vessel; a second portion of the inner surface extending from the aperture to the substrate; and a third portion of the inner surface extending from the first portion to the substrate.

A twenty-seventh aspect is a cell culture vessel according to the twenty-sixth aspect, where each microcavity of the plurality of microcavities includes a concave surface defining a well and an opening defining a path from the cell culture chamber into the well.

A twenty-eighth aspect is a cell culture vessel according to aspect 26 or aspect 27, where the first portion is substantially perpendicular to the axis of the vessel.

A twenty-ninth aspect is a cell culture vessel according to any one of aspects 26-28, where the first portion and the third portion define a non-planar boundary portion of the cell culture chamber.

A thirtieth aspect is a cell culture vessel according to any one of aspects 26-29, where the third portion includes a stepped profile.

A thirty-first aspect is a cell culture vessel according to any one of aspects 26-29, where the third portion includes an inclined profile.

A thirty-second aspect is a cell culture vessel according to any one of aspects 26-31, further including a baffle extending from the second portion of the inner surface, where the baffle includes a major surface obstructing a path defined between the aperture and the substrate.

In thirty-third aspect, a method of culturing cells in the cell culture vessel of any one of aspects 26-32 includes passing liquid through the aperture from outside the vessel into the cell culture chamber, thereby providing a predetermined amount of liquid in the cell culture chamber.

A thirty-fourth aspect is a method of culturing cells according to aspect 33, including containing the predetermined amount of liquid in a region of the cell culture chamber without liquid of the predetermined amount of liquid contacting one or more microcavities of the plurality of microcavities.

A thirty-fifth aspect is a method of culturing cells according to aspect 34, where liquid of the predetermined amount of liquid contacts the first portion and the third portion while containing the predetermined amount of liquid in the region of the cell culture chamber without liquid of the predetermined amount of liquid contacting one or more microcavities of the plurality of microcavities.

A thirty-sixth aspect is a method of culturing cells according to aspect 34 or aspect 35, where the axis of the vessel extends substantially in the direction of gravity while containing the predetermined amount of liquid in the region of the cell culture chamber without liquid of the predetermined amount of liquid contacting one or more microcavities of the plurality of microcavities.

A thirty-seventh aspect is a method of culturing cells according to any one of aspects 34-36, including moving the vessel after containing the predetermined amount of liquid in the region of the cell culture chamber without liquid of the predetermined amount of liquid contacting one or more microcavities of the plurality of microcavities to cause at least a portion of the predetermined amount of liquid to flow from the region over the substrate along the length of the cell culture chamber and deposit in at least one microcavity of the plurality of microcavities.

A thirty-eighth aspect is a method of culturing cells according to aspect 37, including culturing cells in the at least one microcavity of the plurality of microcavities after depositing the at least a portion of the predetermined amount of liquid in the at least one microcavity.

A thirty-ninth aspect is a method of culturing cells according to aspect 38, where the axis of the vessel is substantially perpendicular relative to the direction of gravity while culturing cells in the at least one microcavity of the plurality of microcavities.

In a fortieth aspect, a method of culturing cells includes passing liquid through an aperture in a wall of a vessel from outside the vessel into a cell culture chamber of the vessel defined by an inner surface of the wall and a substrate including a plurality of microcavities, thereby providing a predetermined amount of liquid in a region of the cell culture chamber; and containing the predetermined amount of liquid in the region of the cell culture chamber without liquid of the predetermined amount of liquid contacting one or more microcavities of the plurality of microcavities.

A forty-first aspect is a method of culturing cells according to aspect 40, including moving the vessel to cause at least a portion of the predetermined amount of liquid to flow from the region over the substrate and deposit in at least one microcavity of the plurality of microcavities.

A forty-second aspect is a method of culturing cells according to aspect 41, including culturing cells in the at least one microcavity of the plurality of microcavities after depositing the at least a portion of the predetermined amount of liquid in the at least one microcavity.

In a forty-third aspect, a cell culture vessel includes a substrate including a plurality of microcavities; a wall, the substrate and an inner surface of the wall define a cell culture chamber of the vessel; an aperture extending through the wall in fluid communication with the cell culture chamber; a first portion of the inner surface positioned opposite the aperture along an axis of the vessel, where the substrate spans a length of the cell culture chamber that extends along the axis of the vessel; a second portion of the inner surface extending from the aperture to the substrate; and a baffle extending from the second portion, where the baffle includes a major surface obstructing a path defined between the aperture and the substrate.

A forty-fourth aspect is a cell culture vessel according to aspect 43, where each microcavity of the plurality of microcavities includes a concave surface defining a well and an opening defining a path from the cell culture chamber into the well.

A forty-fifth aspect is a cell culture vessel according to aspect 43 or aspect 44, where the major surface of the baffle is substantially perpendicular to the axis of the vessel.

A forty-sixth aspect is a cell culture vessel according to aspect 43 or aspect 44, where the major surface of the baffle includes a convex profile.

A forty-seventh aspect is a cell culture vessel according to aspect 43 or aspect 44, where the major surface of the baffle includes a concave profile.

A forty-eighth aspect is a cell culture vessel according to any one of aspects 43-47, where at least a portion of a free end of the baffle is spaced a distance from the inner surface of the wall.

In a forty-ninth aspect, a method of culturing cells in the cell culture vessel of any one of aspects 43-48, includes adding material into the cell culture chamber by inserting a dispensing-port into the aperture, and then dispensing material from the dispensing-port into the cell culture chamber.

A fiftieth aspect is a method of culturing cells according to aspect 49, including culturing cells in at least one microcavity of the plurality of microcavities while dispensing material from the dispensing-port into the cell culture chamber.

A fifty-first aspect is a method of culturing cells according to aspect 49 or aspect 25, including removing material from the cell culture chamber by inserting a collecting-port into the aperture, and then collecting material from the cell culture chamber with the collecting-port.

A fifty-second aspect is a method of culturing cells according to aspect 51, including culturing cells in at least one microcavity of the plurality of microcavities while collecting material from the cell culture chamber with the collecting-port.

In a fifty-third aspect, a method of culturing cells includes inserting a dispensing-port into an aperture in a wall of a vessel; flowing material along a first flow path in a cell culture chamber of the vessel defined by an inner surface of the wall and a substrate including a plurality of microcavities by dispensing material from the dispensing-port, thereby adding material from outside the vessel into the cell culture chamber; and obstructing the flow of material along the first flow path.

What is claimed is:

1. A cell culture vessel comprising:
    at least one cell culture chamber, having a bottom, a top and sidewalls;
    a base defining a support plane extending in a first direction and a second direction perpendicular to the first direction;
    wherein the bottom, the top and the sidewalls each have surfaces facing the inside of the cell culture chamber;
    wherein at least the bottom surface of the cell culture chamber comprises an array of microcavities;
    an inlet in a top of the vessel providing access to the cell culture chamber on one side of the vessel;
    an outlet in a bottom of the vessel providing access to each cell culture chamber on the opposite side of the vessel;
    wherein the first direction of the support plane of the base is along the axis between the inlet and the outlet;
    wherein the second direction of the support plane of the base is perpendicular to the axis between the inlet and the outlet;
    wherein the bottom surface of the cell culture chamber defines a substrate plane which is at a first angle relative to the first direction of the substrate plane and a second angle relative to the second direction of the substrate plane; and,
    wherein an absolute value of at least one of the first angle and the second angle is greater than zero.

2. The cell culture vessel of claim 1, wherein an absolute value of the first angle or the second angle or both is from about 1° to about 30°.

3. The cell culture vessel of claim 1, wherein an absolute value of the first plane angle is about 5°, wherein an absolute value of the second plane angle is about 5°, or the absolute value of both the first plane angle and the second plane angle is about 5°.

4. The cell culture vessel of claim 1, wherein the inlet is in the top corner of the vessel.

5. The cell culture vessel of claim 4 wherein the outlet is in a bottom corner of the vessel opposite the inlet top corner.

6. The cell culture vessel of claim 1, comprising at least two cell culture chambers stacked one above the other:
    wherein the inlet is fluidly connected to each cell culture chamber via an inlet manifold, and each cell culture chamber has an inlet opening between the cell culture chamber and the inlet manifold; and
    wherein the outlet is fluidly connected to each cell culture chamber via an outlet manifold, and each cell culture chamber has an outlet opening between the cell culture chamber and the outlet manifold.

7. The cell culture vessel of claim 1, wherein the bottom of each of the at least one cell culture chamber comprises gas permeable, liquid impermeable material.

8. The cell culture vessel of claim 7 wherein each cell culture chamber is separated from its next adjacent cell culture chamber by a tracheal space.

9. The cell culture vessel of claim 2 wherein the inlet is in the top corner of the vessel.

10. The cell culture vessel of claim 3 wherein the inlet is in the top corner of the vessel.

11. The cell culture vessel of claim 10 wherein the outlet is in a bottom corner of the vessel opposite the inlet top corner.

12. The cell culture vessel of claim 1 comprising at least two cell culture chambers stacked one above the other.

13. The cell culture vessel of claim 2, comprising at least two cell culture chambers stacked one above the other, wherein the inlet is fluidly connected to each cell culture chamber via an inlet manifold, and each cell culture chamber has an inlet opening between the cell culture chamber and the inlet manifold; and wherein the outlet is fluidly connected to each cell culture chamber via an outlet manifold, and each cell culture chamber has an outlet opening between the cell culture chamber and the outlet manifold.

14. The cell culture vessel of claim 2, comprising at least two cell culture chambers stacked one above the other, wherein the inlet is fluidly connected to each cell culture chamber via an inlet manifold; each cell culture chamber has an inlet opening between the cell culture chamber and the inlet manifold; and wherein the outlet is fluidly connected to each cell culture chamber via an outlet manifold, and each cell culture chamber has an outlet opening between the cell culture chamber and the outlet manifold.

15. The cell culture vessel of claim 3, comprising at least two cell culture chambers stacked one above the other, wherein the inlet is fluidly connected to each cell culture chamber via an inlet manifold; each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

16. The cell culture vessel of claim 9, comprising at least two cell culture chambers stacked one above the other, wherein the inlet is fluidly connected to each cell culture chamber via an inlet manifold, and each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

17. The cell culture vessel of claim 10, comprising at least two cell culture chambers stacked one above the other, wherein the inlet is fluidly connected to each cell culture chamber via an inlet manifold, and each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

18. The cell culture vessel of claim 11, comprising at least two cell culture chambers stacked one above the other, wherein the inlet is fluidly connected to each cell culture chamber via an inlet manifold, and each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

19. The cell culture vessel of claim 2, wherein the inlet is in the top corner of the vessel.

20. The cell culture vessel of claim 3, wherein the inlet is in the top corner of the vessel.

21. The cell culture vessel of claim 19, wherein the outlet is in a bottom corner of the vessel opposite the inlet top corner.

22. The cell culture vessel of claim 20, wherein the outlet is in a bottom corner of the vessel opposite the inlet top corner.

23. The cell culture vessel of claim 18, comprising at least two cell culture chambers stacked one above the other, wherein the inlet is fluidly connected to each cell culture chamber via an inlet manifold; each cell culture chamber has an inlet opening between the cell culture chamber and the inlet manifold; and wherein the outlet is fluidly connected to each cell culture chamber via an outlet manifold, and each cell culture chamber has an outlet opening between the cell culture chamber and the outlet manifold.

24. The cell culture vessel of claim 19, comprising at least two cell culture chambers stacked one above the other, wherein the inlet is fluidly connected to each cell culture chamber via an inlet manifold; each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

25. The cell culture vessel of claim 20, comprising at least two cell culture chambers stacked one above the other, wherein the inlet is fluidly connected to each cell culture chamber via an inlet manifold, and each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

26. The cell culture vessel of claim 21, comprising at least two cell culture chambers stacked one above the other, wherein the inlet is fluidly connected to each cell culture chamber via an inlet manifold, and each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

27. The cell culture vessel of claim 22, comprising at least two cell culture chambers stacked one above the other, wherein the inlet is fluidly connected to each cell culture chamber via an inlet manifold, and each cell culture chamber has an inlet opening between the cell culture chamber and the inlet manifold and wherein the outlet is fluidly connected to each cell culture chamber via an outlet manifold, and each cell culture chamber has an outlet opening between the cell culture chamber and the outlet manifold.

28. A method of culturing cells in the cell culture vessel of claim 1, comprising:
   introducing liquid containing cells and media in the cell culture chambers through the inlet;
   allowing cells to settle into the microcavities by gravity; and,
   culturing cells.

29. The method of claim 28, further comprising flowing liquid into the vessel through the inlet, the cell culture chamber(s), and out of the vessel through the outlet while culturing the cells.

* * * * *